US011369480B2

(12) United States Patent
Roche et al.

(10) Patent No.: US 11,369,480 B2
(45) Date of Patent: Jun. 28, 2022

(54) HUMERAL TRAYS WITH TUBEROSITY AUGMENTS SUFFICIENTLY DESIGNED TO IMPROVE JOINT MECHANICS

(71) Applicant: EXACTECH, INC., Gainesville, FL (US)

(72) Inventors: Christopher Roche, Gainesville, FL (US); Howard David Routman, North Palm Beach, FL (US); Raymond Anthony Klug, Long Beach, CA (US); Corey Mitchell Gaydos, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 632 days.

(21) Appl. No.: 15/523,181

(22) PCT Filed: Oct. 29, 2015

(86) PCT No.: PCT/US2015/057999
§ 371 (c)(1),
(2) Date: Apr. 28, 2017

(87) PCT Pub. No.: WO2016/069867
PCT Pub. Date: May 6, 2016

(65) Prior Publication Data
US 2017/0333197 A1  Nov. 23, 2017

Related U.S. Application Data

(60) Provisional application No. 62/073,281, filed on Oct. 31, 2014.

(51) Int. Cl.
*A61F 2/40* (2006.01)
*A61F 2/30* (2006.01)

(52) U.S. Cl.
CPC ........ *A61F 2/4059* (2013.01); *A61F 2/30734* (2013.01); *A61F 2/40* (2013.01);
(Continued)

(58) Field of Classification Search
CPC ................ A61F 2/4059; A61F 2/30734; A61F 2002/30616; A61F 2002/30736; A61F 2002/4066; A61F 2002/4085
See application file for complete search history.

(56) References Cited

U.S. PATENT DOCUMENTS

2010/0292802 A1   11/2010   Borowsky
2012/0290098 A1   11/2012   Mutchler et al.
(Continued)

FOREIGN PATENT DOCUMENTS

WO     2007082925 A2    7/2007

OTHER PUBLICATIONS

International Search Report for PCT Application No. PCT/US2015/057999, dated Jan. 8, 2016.
(Continued)

*Primary Examiner* — Jerrah Edwards
*Assistant Examiner* — Christine L Nelson
(74) *Attorney, Agent, or Firm* — Greenberg Traurig, LLP

(57) ABSTRACT

Disclosed is a prosthetic augment designed to reconstruct a lateral tuberosity shape of a humerus in a subject having proximal bone loss that includes a humeral adapter tray configured to connect a humeral liner of a reverse shoulder prosthesis to a humeral stem of the reverse shoulder prosthesis and an augment member having a first face adapted for contacting the humeral stem of the reverse shoulder prosthesis and a second face adapted for contacting an underside of a muscle, wherein at least a portion of the second face includes a bulbous surface adapted to alter a wrapping angle of the muscle around the lateral tuberosity,
(Continued)

and wherein the second face has a radius of curvature selected from one of a constant radius of curvature or a variable radius of curvature.

20 Claims, 35 Drawing Sheets

(52) U.S. Cl.
CPC .............. *A61F 2002/30433* (2013.01); *A61F 2002/30604* (2013.01); *A61F 2002/30616* (2013.01); *A61F 2002/30736* (2013.01); *A61F 2002/4022* (2013.01); *A61F 2002/4066* (2013.01); *A61F 2002/4085* (2013.01)

(56) References Cited

U.S. PATENT DOCUMENTS

| | | | | |
|---|---|---|---|---|
| 2013/0325131 | A1* | 12/2013 | Roche .................. | A61F 2/4081 623/19.13 |
| 2014/0039633 | A1* | 2/2014 | Roche .................. | A61F 2/4081 623/19.13 |
| 2014/0058526 | A1* | 2/2014 | Meridew .............. | A61F 2/3094 623/23.5 |

OTHER PUBLICATIONS

European Search Report (EP 15855048.3) dated Jun. 11, 2018, 6 pages).

\* cited by examiner

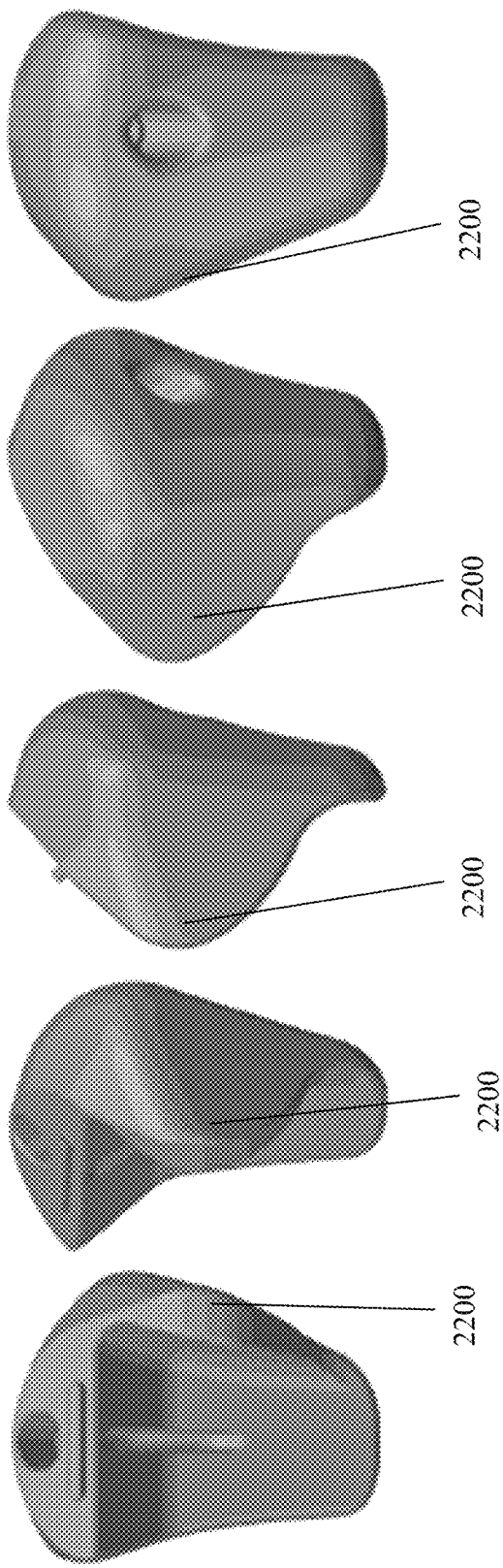

HUMERAL TRAYS WITH TUBEROSITY AUGMENTS SUFFICIENTLY DESIGNED TO IMPROVE JOINT MECHANICS

CROSS REFERENCE TO RELATED APPLICATIONS

This is a 371 National Phase of International Application No. PCT/US2015/057999, filed Oct. 29, 2015, which claims the benefit of U.S. Provisional Application No. 62/073,281, filed on Oct. 31, 2014, which is incorporated by reference herein in its entirety.

BACKGROUND

Muscles generate straight line forces that are converted to torques in proportion to their perpendicular distance between the joint center of rotation (CoR) and the muscle's line of action. This perpendicular distance is termed the muscle moment arm; thus, a 50% larger moment arm implies a 50% lower force required by a particular muscle to induce a given torque or a particular motion. The location of the moment arm relative to the joint CoR determines the type of motion the muscle will create. In the shoulder, these motions are abduction/adduction (in the scapular/coronal plane and/or in the transverse plane), internal/external rotation (rotation of long axis of humerus), and flexion/extension (in the sagittal plane). The greater the muscle's moment arm, the greater capacity for that muscle to generate the torque required for motion and to support external loads. The tradeoff for a larger moment arm is that the muscle then requires a greater excursion (i.e. more muscle shortening to generate a given amount of motion). It should be recognized that a muscle's moment arm is only one component of a muscle's ability to generate torque, other factors include the muscle's physiologic cross sectional area, architecture, neural activity, and its length-tension relationship.

SUMMARY

Humeral trays with tuberosity augments sufficiently designed to improve joint mechanics are disclosed herein. In an embodiment, "improve muscle mechanics" means the ability to increase a muscle's moment arm, and/or increase the muscle's length/tension, and/or alter the muscle's line of action, and/or increase the muscle's wrapping.

According to aspects illustrated herein, there is disclosed a prosthetic augment sufficiently designed to reconstruct a lateral tuberosity shape of a humerus in a subject having proximal bone loss that includes a humeral adapter tray configured to connect a humeral liner of a reverse shoulder prosthesis to a humeral stem of the reverse shoulder prosthesis; and an augment member having a first face adapted for contacting the humeral stem of the reverse shoulder prosthesis; and a second face adapted for contacting an underside of a muscle, wherein at least a portion of the second face includes a bulbous surface adapted to alter a wrapping angle of the muscle around the lateral tuberosity, and wherein the second face has a radius of curvature selected from one of a constant radius of curvature or a variable radius of curvature. In an embodiment, the humeral adapter tray and the augment member act as a single, monolithic, device. In an embodiment, the humeral adapter tray and the augment member are two separate, modular components. In an embodiment, the second face has a constant radius and the bulbous surface is a sphere. In an embodiment, the second face has a variable radius of curvature and the bulbous surface is sufficiently elongated to accommodate the anatomic variance of the lateral tuberosity. In an embodiment where the bulbous surface is sufficiently elongated, a first thickness is defined between the first face and the second face at a first position on the augment member, the first thickness ranging from about 1 mm to less than about 5 mm, and a second thickness is defined between the first face and the bulbous surface of the second face, the second thickness ranging from about 7 mm to about 50 mm.

In an embodiment, a patient with proximal humeral bone loss having a reverse shoulder prosthesis that includes a humeral adapter tray/tuberosity augment device of the present disclosure, will experience improved function of the shoulder joint by recreating the shape/contour of the lateral tuberosity of the proximal humeral bone. In an embodiment, a patient with proximal humeral bone loss having a reverse shoulder prosthesis that includes a humeral adapter tray/tuberosity augment device of the present disclosure, will experience improved stability of the shoulder joint by recreating the shape/contour of the lateral tuberosity of the proximal humeral bone. In an embodiment, a patient with proximal humeral bone loss having a reverse shoulder prosthesis that includes a humeral adapter tray/tuberosity augment device of the present disclosure, will experience reduced probability of deltoid scarring by restoring a smooth surface for the muscle to slide/articulate against.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 16A illustrates a humeral adapter tray secured to the Equinoxe® anatomic humeral stem to reconstruct the lateral tuberosity shape/contour in patients with proximal bone loss. FIG. 16B illustrates an embodiment of the present invention where the monolithic humeral adapter tray with tuberosity augment of FIG. 10 is secured to the Equinoxe® anatomic humeral stem to reconstruct the lateral tuberosity shape/contour in patients with proximal bone loss.

FIG. 17B is a cross-sectional view showing a cutout to permit attachment of the humeral tray to all sizes of humeral stems (from sizes 6 to 17 mm);

FIG. 18A illustrate a humeral adapter tray secured to the Equinoxe® anatomic humeral stem to reconstruct the lateral tuberosity shape/contour in patients with proximal bone loss. FIG. 18B illustrates an embodiment of the present invention where the modular humeral adapter tray/tuberosity augment of FIG. 11 is secured to the Equinoxe® anatomic humeral stem to reconstruct the lateral tuberosity shape/contour in patients with proximal bone loss.

FIG. 19A illustrates a humeral adapter tray secured to the Equinoxe® fracture humeral stem to reconstruct the lateral tuberosity shape/contour in patients with proximal bone loss. FIG. 19B illustrates an embodiment of the present invention where the monolithic humeral adapter tray with tuberosity augment of FIG. 10 is secured to the Equinoxe® fracture humeral stem to reconstruct the lateral tuberosity shape/contour in patients with proximal bone loss.

FIG. 20B is a cross-sectional view showing a cutout to permit attachment of tray to all sizes of humeral stems (from sizes 6.5 to 12.5 mm).

FIGS. 22A-22E illustrate five different views of an embodiment of a modular tuberosity augment of the present invention with additional anterior (or posterior) coverage for connection to a modular humeral adapter tray (not pictured) of the present invention.

FIG. 28A illustrates a tuberosity augment having a "thin" thickness. FIG. 28B illustrates a tuberosity augment having a "standard" thickness. FIG. 28C illustrates a tuberosity augment having a "thick" thickness. A tuberosity augment is chosen to selectively lateralize the deltoid and intra-operatively tension the joint.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components (and any size, material and similar details shown in the figures are, of course, intended to be illustrative and not restrictive). Therefore, specific structural and functional details disclosed herein are not to be interpreted as limiting, but merely as a representative basis for teaching one skilled in the art to variously employ the present invention.

Reduced muscle function with arthroplasty is a complicated issue. In the shoulder, prosthetic design parameters can alter the tension of the muscles above or below their normal/native resting length (i.e., the length of the muscles of the native anatomic shoulder in neutral position) and or strategically increase (or decrease) the moment arms of muscles to make them more (or less) important contributor to a given type of motion.

Figure 1:
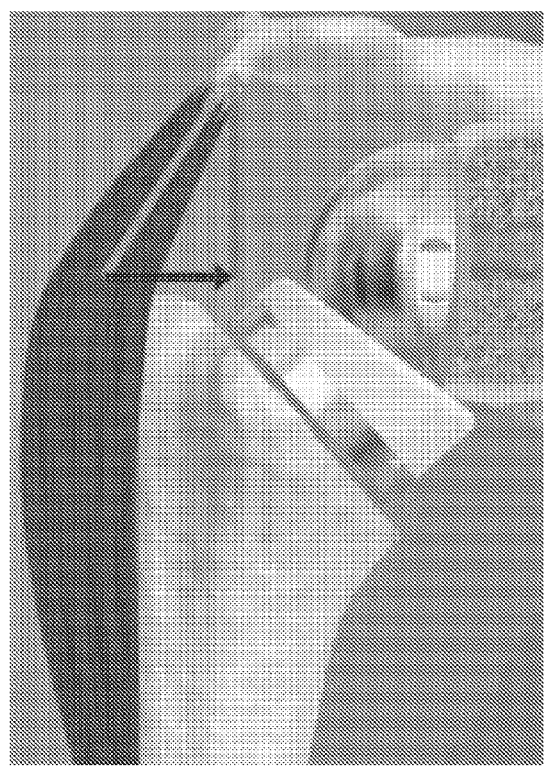
FIG. 1 is a rendition of the middle deltoid wrapping around the greater tuberosity of the shoulder to increase the stability via humeral head compression.

The deltoid is the largest and most important muscle in the shoulder girdle. It is the primary mover in the shoulder, and generates forward elevation in the scapular plane. The deltoid consists of three distinct heads: 1) anterior (anterior acromion and clavicle), 2) middle (lateral margin of the acromion), and 3) the posterior deltoid (scapular spine); and accounts for approximately 20% of the mass of the shoulder muscles. At low levels of abduction, the wrapping of the middle deltoid around the greater tuberosity of the humeral head (FIG. 1) generates a stabilizing compressive force; however, this compressive force is small relative to that generated by the rotator cuff.

Changing the joint center of rotation with arthroplasty (specifically, with a reverse shoulder in which the inversion of the anatomic concavities and the inferior and medial shift of the center of rotation) dramatically alters the relationship of each (shoulder) muscle to its normal physiologic function. In the shoulder, medially shifting the center of rotation increases the length of the anterior, middle, and posterior deltoid abduction moment arms and lengthens the anterior, middle, and posterior deltoid allowing them to contribute more toward abduction. These larger abductor moment arms enhance the capacity of the deltoid to elevate the arm in the scapular and coronal planes, compensating for the impaired function of the supraspinatus and the superior portions of the subscapularis and infraspinatus rotator cuff muscles which are typically involved in the indicated pathology. Medially shifting the center of rotation also translates the humerus medially which increases the laxity of any remaining rotator cuff muscles and also leads to impingement of the humerus with the scapular neck at low elevation (i.e. scapular notching).

Restoring the lateral position of the humeral tuberosities is important to tension the remaining rotator cuff muscles in a more natural physiologic manner and offers the potential to better restore rotational strength. While over-tensioning these muscles may offer the possibility of improved resting tone/tension, it may also make it more difficult to repair following tenotomy (in the case of the subscapularis).

Being able to improve the mechanics of a particular muscle (without impairing any other muscle) by strategically increasing its moment arm or alter its line of action and increase its wrapping may improve function and potentially eliminate the need for muscle transfers; especially in difficult pathologies like rotator cuff tear arthropathy or revision arthroplasty in which reverse shoulder arthroplasty is typically indicated.

Figure 2:
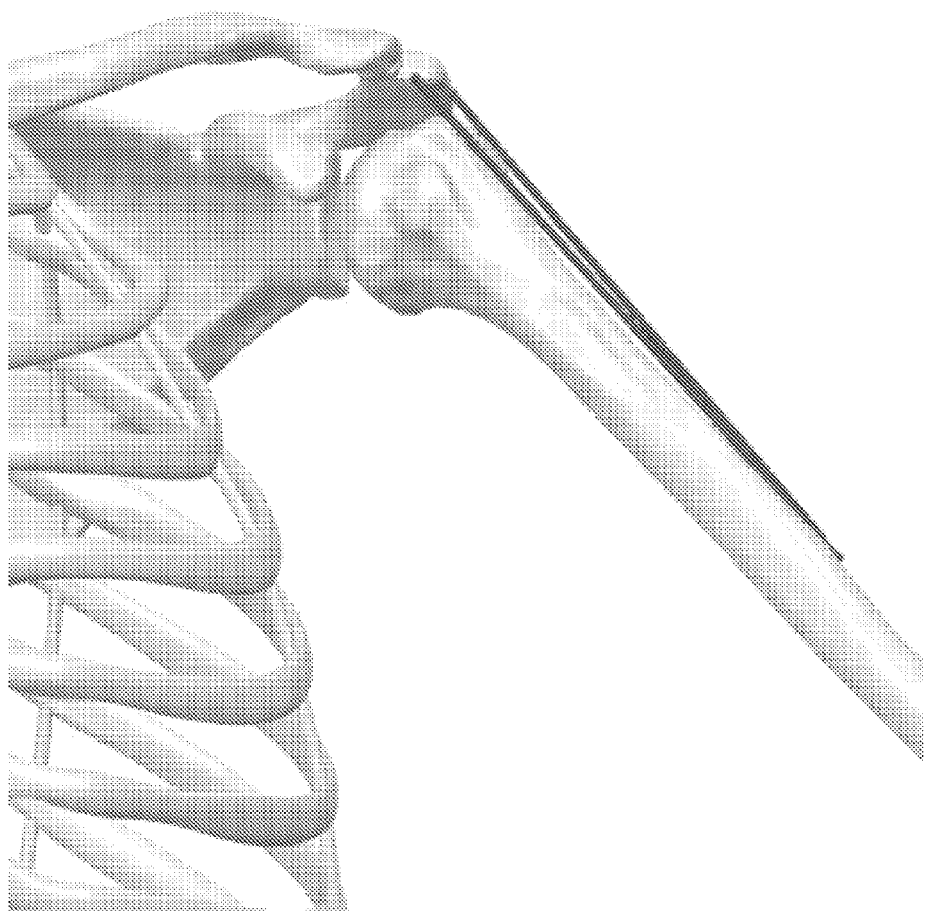
FIG. 2 is a computer model of the normal shoulder abducted to 48 degrees relative to a fixed scapula in which the middle deltoid no longer wraps the greater tuberosity of the humeral head and therefore no longer imparts a stabilizing compressive force to the glenoid.
Figure 3:
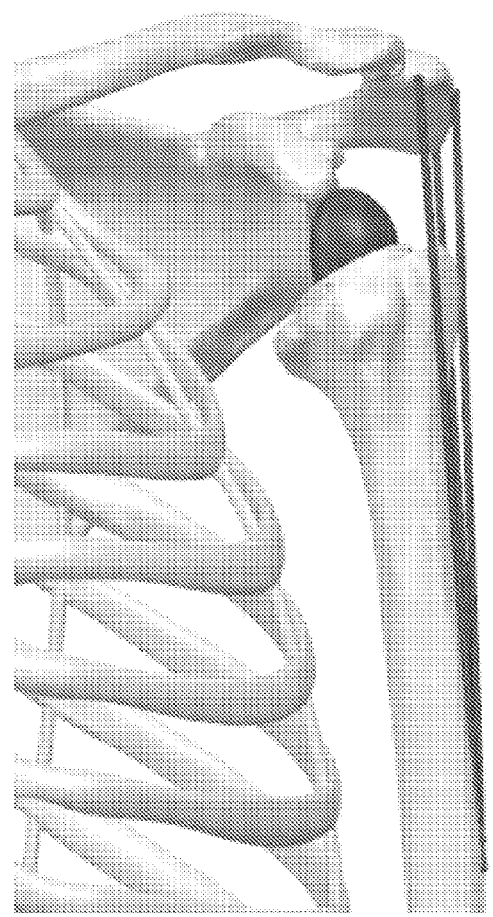
FIG. 3 is a computer model of a 36 mm Grammont reverse shoulder abducted to 8 degrees relative to a fixed scapula in which the middle deltoid no longer wraps the greater tuberosity of the humeral head and therefore no longer imparts a stabilizing compressive force to the glenoid.
Figure 4:
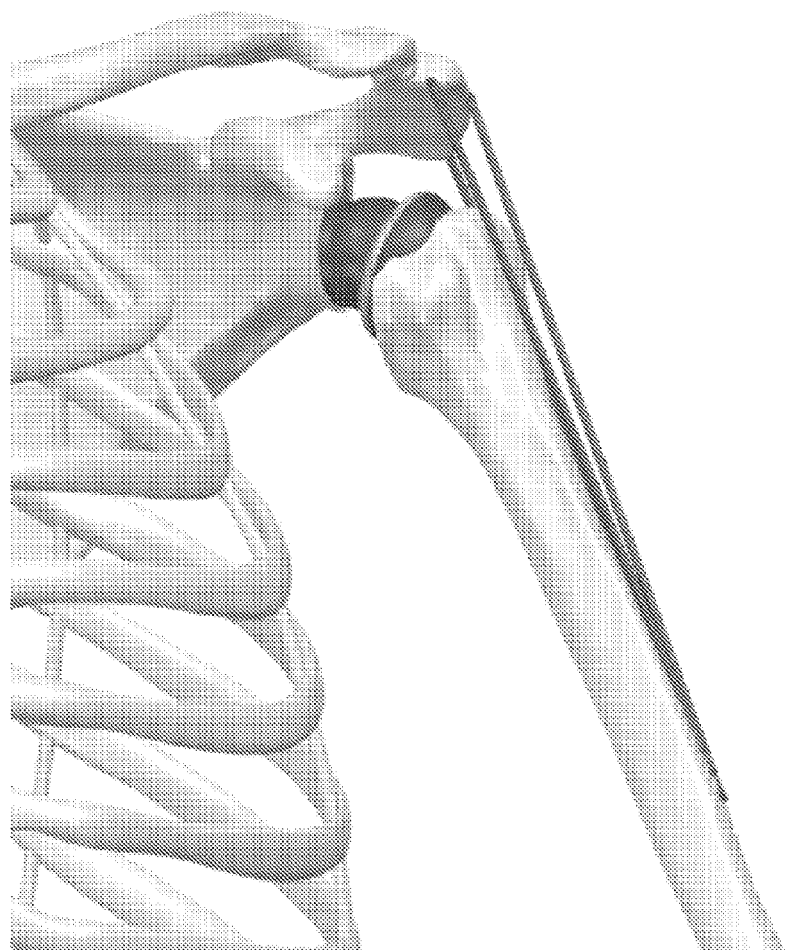
FIG. 4 is a computer model of a 32 mm Encore Reverse® shoulder abducted to 28 degrees relative to a fixed scapula in which the middle deltoid no longer wraps the greater tuberosity of the humeral head and therefore no longer imparts a stabilizing compressive force to the glenoid.
Figure 5:
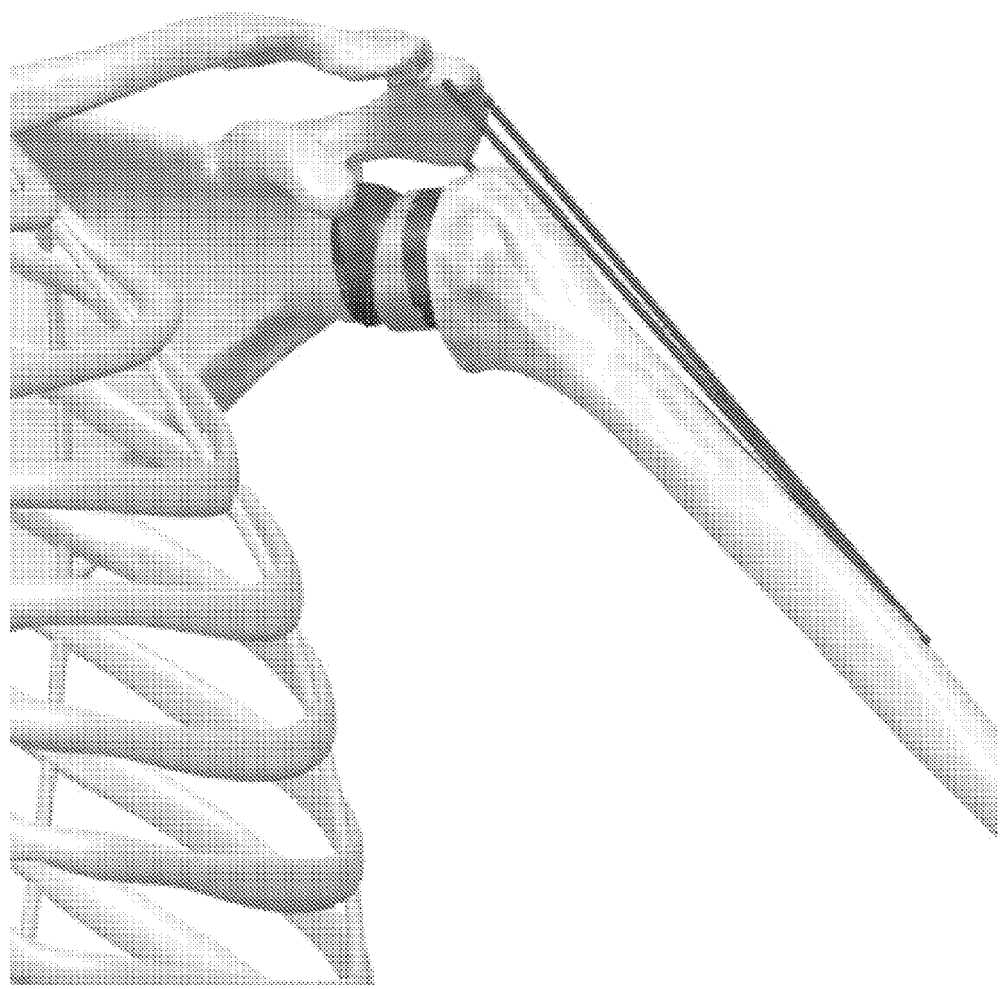
FIG. 5 is a computer model of a 38 mm Equinoxe® reverse shoulder abducted to 40 degrees relative to a fixed scapula in which the middle deltoid no longer wraps the greater tuberosity of the humeral head and therefore no longer imparts a stabilizing compressive force to the glenoid.

As described in Table 1 below, deltoid wrapping can be altered by different prosthesis designs (Grammont reverse shoulder, Encore Reverse® shoulder, and Equinoxe® reverse shoulder), different orientations (e.g. changing humeral retroversion and or changing the tilt of the implant), and/or implanting the device in a scapula with varying scapular morphology or wear patterns (e.g. medial glenoid wear). The results presented in Table 1 were calculated from a computer model which simulates muscle lines of action in the shoulder during various arm positions. FIG. 2 is a computer model illustrating the arm abduction in which the middle deltoid ceases to wrap the humeral head greater tuberosity in the normal shoulder (i.e. no prosthesis) at 48° abduction in the scapular plane (relative to a fixed scapula). FIGS. 3-5 are computer models illustrating the same deltoid wrapping phenomenon with varying reverse shoulder prosthesis designs (36 mm Grammont reverse shoulder abducted to 8° relative to a fixed scapula (FIG. 3), 32 mm Encore Reverse® shoulder abducted to 28° relative to a fixed scapula (FIG. 4), and 38 mm Equinoxe® reverse shoulder abducted to 40° relative to a fixed scapula, (FIG. 5)). In FIGS. 3-5 the middle deltoid no longer wraps the greater tuberosity of the humeral head and therefore no longer imparts a stabilizing compressive force to the glenoid.

TABLE 1

Wrapping of Middle Deltoid Around Greater Tuberosity (computer modeling study)

| | Abduction where deltoid doesn't wrap tuberosity |
|---|---|
| Normal Shoulder | 48° |
| 36 Grammont, 20° retroversion | 8° |
| 32 Encore Reverse ®, 20° retroversion | 28° |

TABLE 1-continued

Wrapping of Middle Deltoid Around Greater Tuberosity (computer modeling study)

Figure 6:
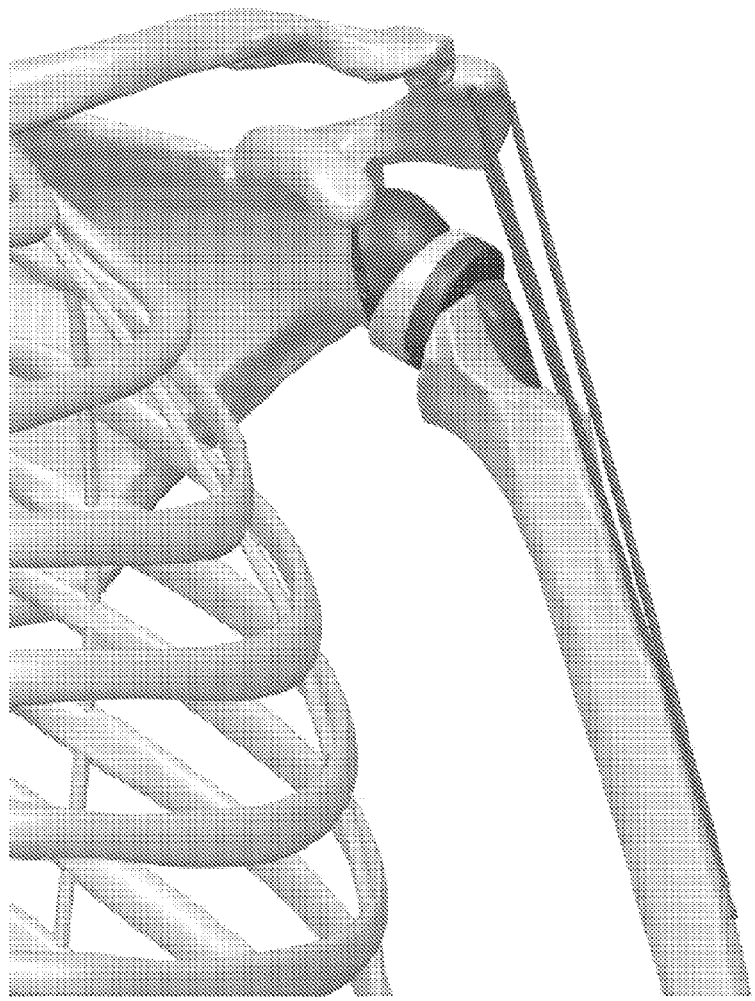
FIG. 6 is a computer model of the 38 mm Equinoxe reverse shoulder with proximal humeral bone loss abducted to 20 degrees relative to a fixed scapula in which the middle deltoid no longer wraps the lateral humerus and therefore no longer imparts a stabilizing compressive force to the glenoid.
Figure 7:
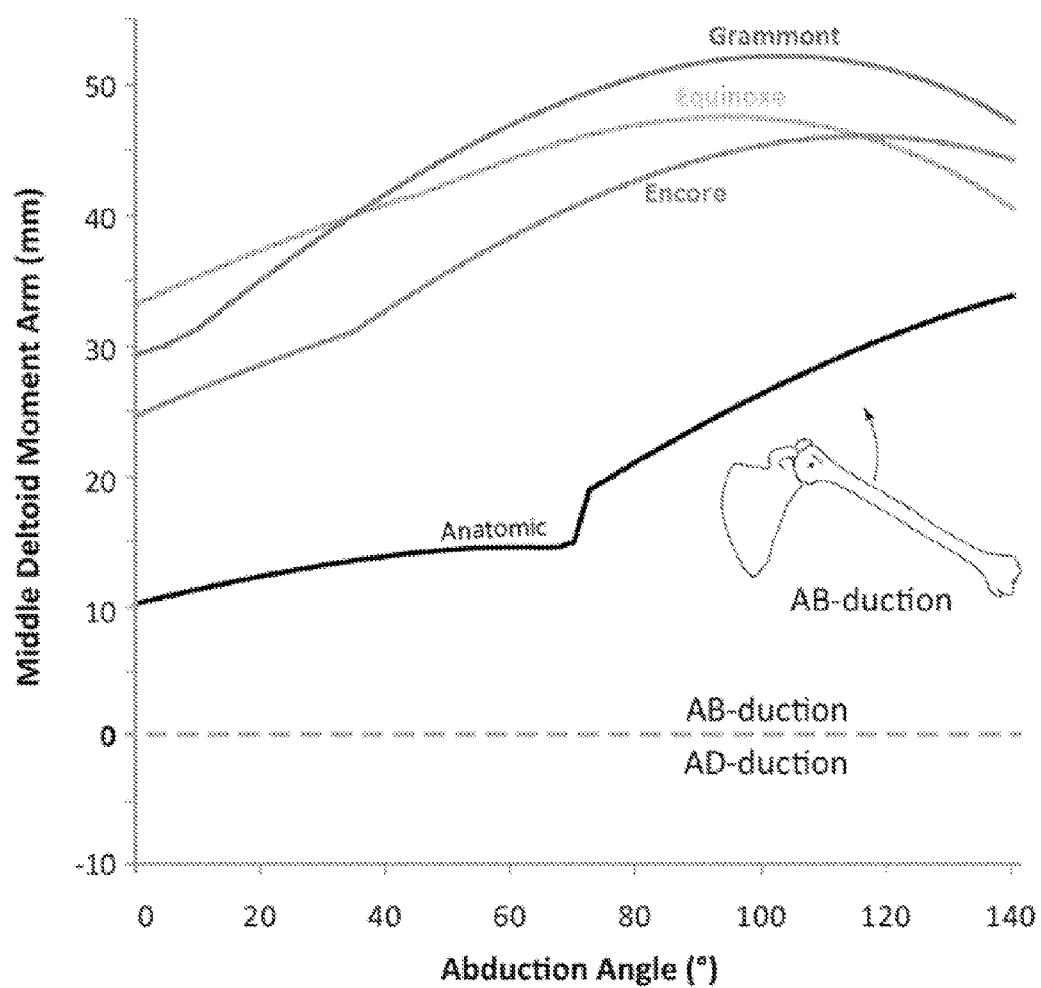
FIG. 7 is a graph showing abduction moment arm for the middle deltoid through 140° of abduction for the normal anatomic shoulder and for three (3) reverse shoulder designs (Grammont, Encore Reverse® and Equinoxe®).
Figure 8A:
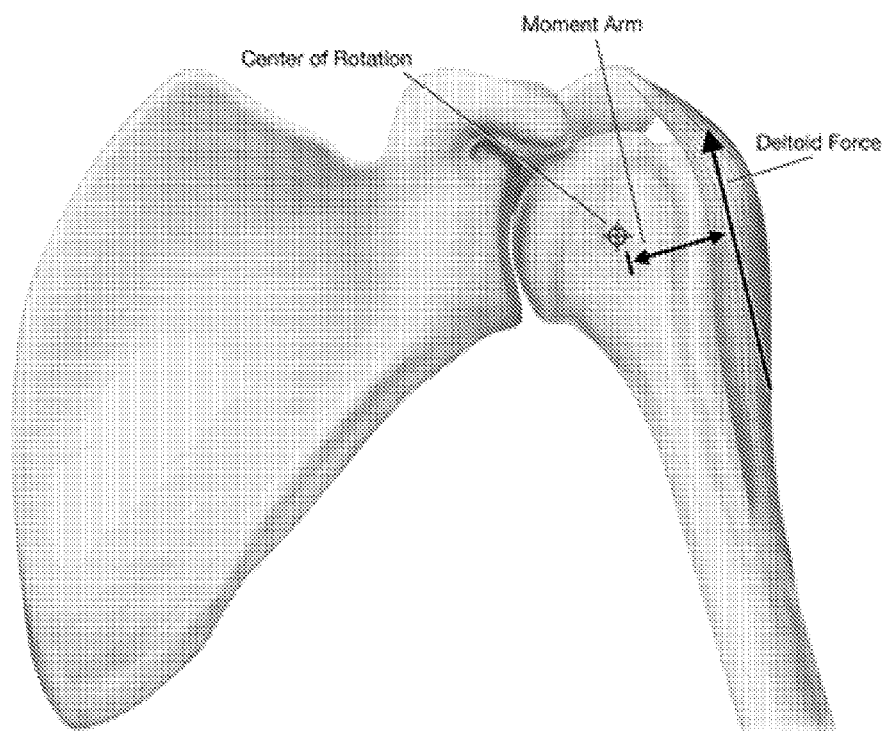
FIGS. 8A-8D are computer models comparing middle deltoid abduction moment arms between the normal shoulder (FIG. 8A) and 3 different reverse shoulder designs: Grammont (FIG. 8B), Encore Reverse® (FIG. 8C), and Equinoxe® (FIG. 8D).
Figure 8B:
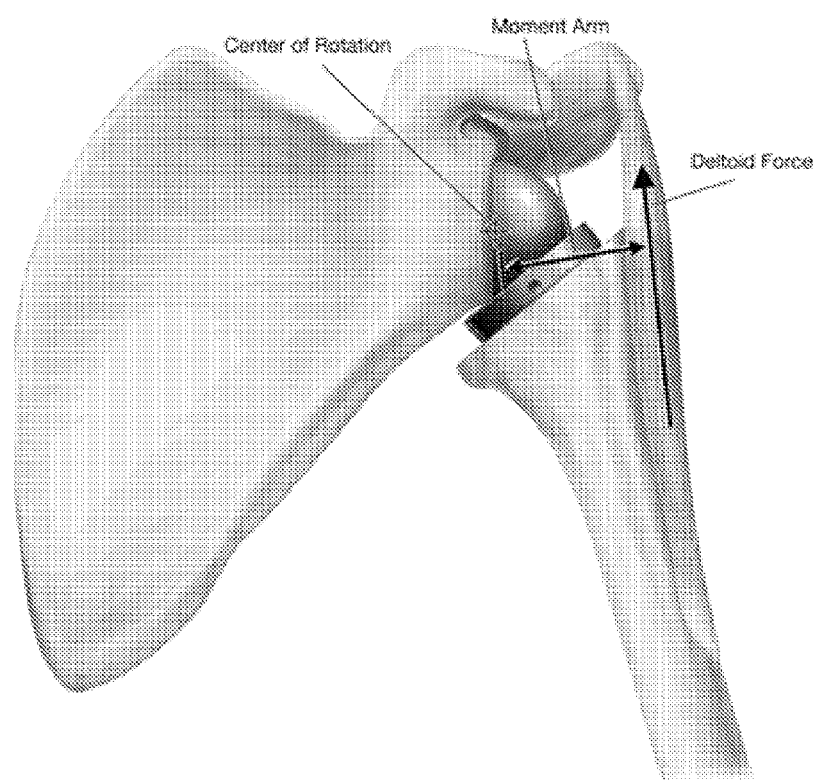
Figure 8C:
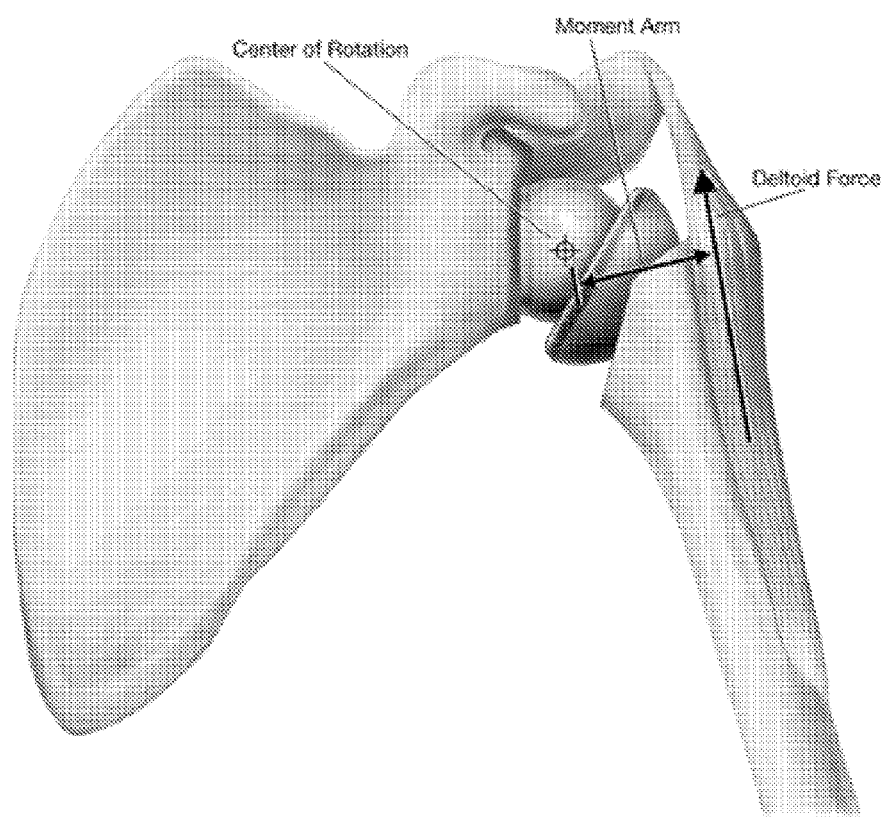
Figure 8D:
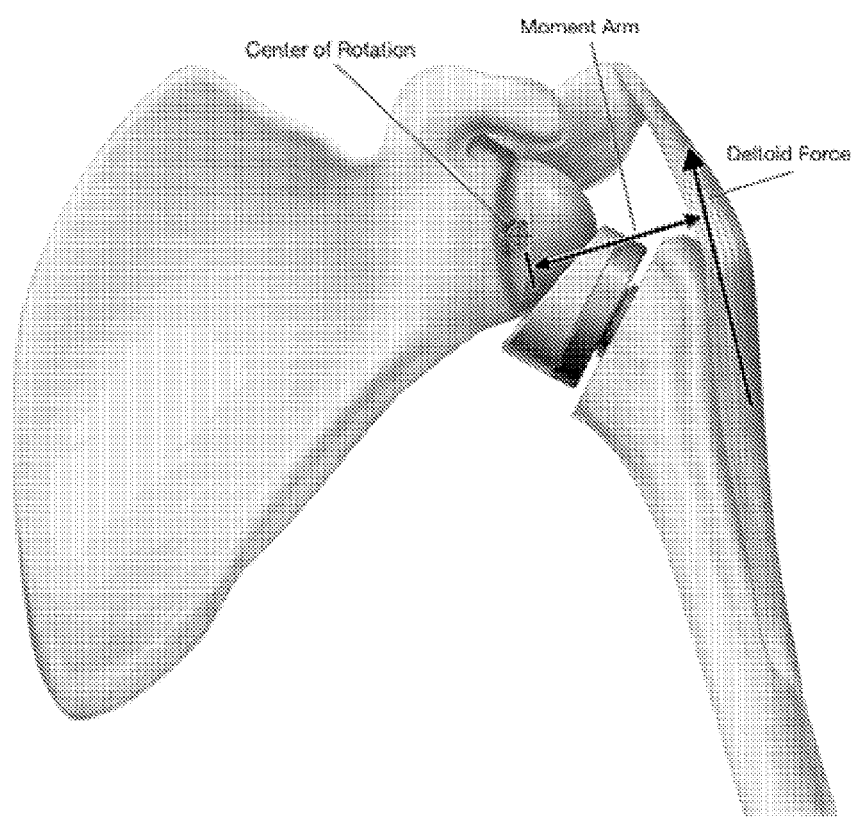

| | Abduction where deltoid doesn't wrap tuberosity |
|---|---|
| 38 Equinoxe ®, 20° retroversion | 40° |
| 36 Grammont, 0° retroversion | 16° |
| 36 Grammont, 40° retroversion | 7° |
| 36 Grammont, 15° tilt | 7° |
| 32 Encore Reverse ®, 15° tilt | 21° |
| 36 Grammont, 10 mm medial wear | −1° |
| 32 Encore Reverse ®, 10 mm medial wear | 12° |
| 38 Equinoxe ®, 10 mm medial wear | 18° |
| 38 Equinoxe with Proximal Bone Loss (FIG. 6) | 20° |

As described in FIG. 7 and FIGS. 8A-8D, the middle deltoid abductor moment arm is significantly increased with reverse shoulder arthroplasty. However, the magnitude of the middle deltoid moment arm is altered by different prosthesis designs (Grammont reverse shoulder, Encore Reverse® shoulder, vs Equinoxe® reverse shoulder) and changes as a function of humeral elevation. Proximal humeral bone loss would also reduce the size of the deltoid abductor moment arms for the normal shoulder and each reverse shoulder design.

Figure 9:
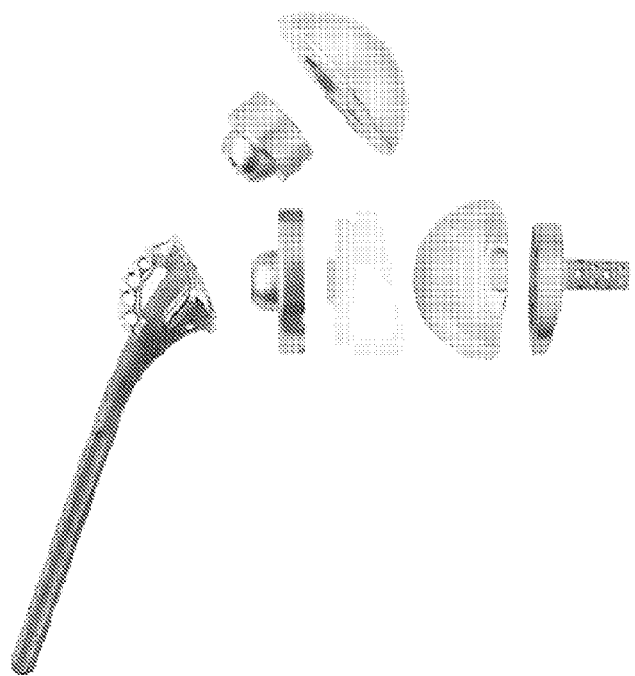
FIG. 9 illustrates an embodiment of an Equinoxe® Platform Fracture Stem. The platform fracture stem is cemented into the humeral intramedullary (IM) canal as the surgeon secures the less and greater tuberosity fracture fragments around the asymmetric fin with sutures. After securing fracture fragments with sutures back to the stem and humeral shaft, the surgeon either performs a hemiarthroplasty or a reverse shoulder.
Figure 10A:
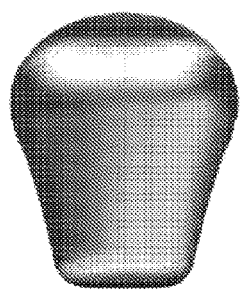
FIGS. 10A-10D illustrate four different views of an embodiment of a monolithic humeral adapter tray with tuberosity augment of the present invention.
Figure 10B:
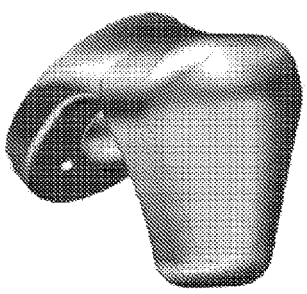
Figure 10C:
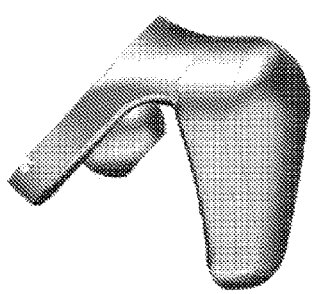
Figure 10D:
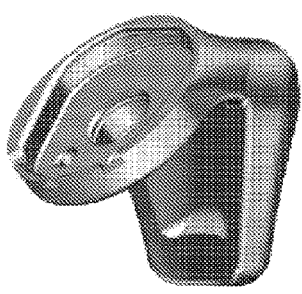
Figure 11A:
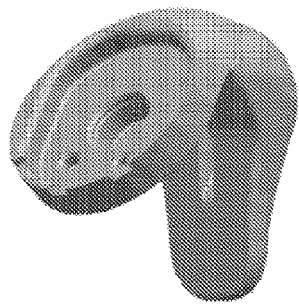
FIGS. 11A-11D illustrate four different views of an embodiment of a modular humeral adapter tray assembled to a modular tuberosity augment (assembled with taper and locking screw) of the present invention.
Figure 11B:
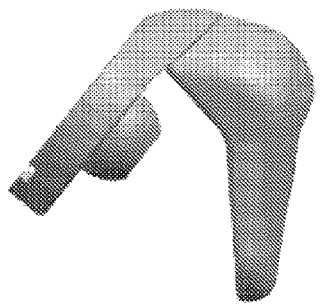
Figure 11C:
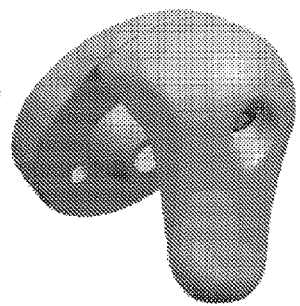
Figure 11D:
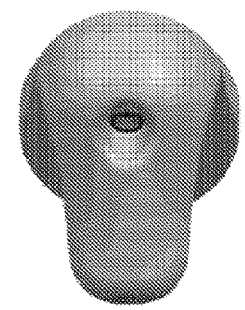

FIG. 9 illustrates an embodiment of an Equinoxe® Platform Fracture Stem manufactured from Exactech, Inc., Gainesville, Fla. The Equinoxe® Platform Fracture Stem is cemented into the humeral intramedullary (IM) canal as the surgeon secures the less and greater tuberosity fracture fragments around the asymmetric fin with sutures. The Equinoxe® Platform Fracture Stem permits the surgeon to reconstruct the fracture around the cemented stem and perform either a hemiarthroplasty or reverse total shoulder. Should the fracture reconstruction fail for the hemiarthroplasty, the hemiarthroplasty would need to be converted to a reverse shoulder (as the greater and tuberosities would resorb and the rotator cuff muscles which attach to the fracture fragments would become nonfunctional). However, should the fracture reconstruction fail for the reverse shoulder, the function and stability of the reverse shoulder would be diminished by the proximal humeral bone loss for the reasons described above (the deltoid is medialized by reduced wrapping around the greater tuberosity/lateral proximal humerus—this medialized deltoid would decrease its tension, reduce its moment arm, reduce its deltoid wrapping and create cosmetic concerns).

FIGS. 10A-10D illustrate four different views of an embodiment of a monolithic humeral adapter tray with tuberosity augment of the present invention. The outer surface of the tuberosity augment includes a lower portion that is substantially a flat surface and an upper portion with a convex curvature configured so as to allow the deltoid muscle to wrap around a greater tuberosity of a humeral head.

FIGS. 11A-11D illustrate four different views of an embodiment of a modular humeral adapter tray assembled to a modular tuberosity augment (assembled with taper and locking screw) of the present invention. The outer surface of the modular tuberosity augment includes a lower portion that is substantially a flat surface and an upper portion with a convex curvature configured so as to allow the deltoid muscle to wrap around a greater tuberosity of a humeral head.

Figure 12:
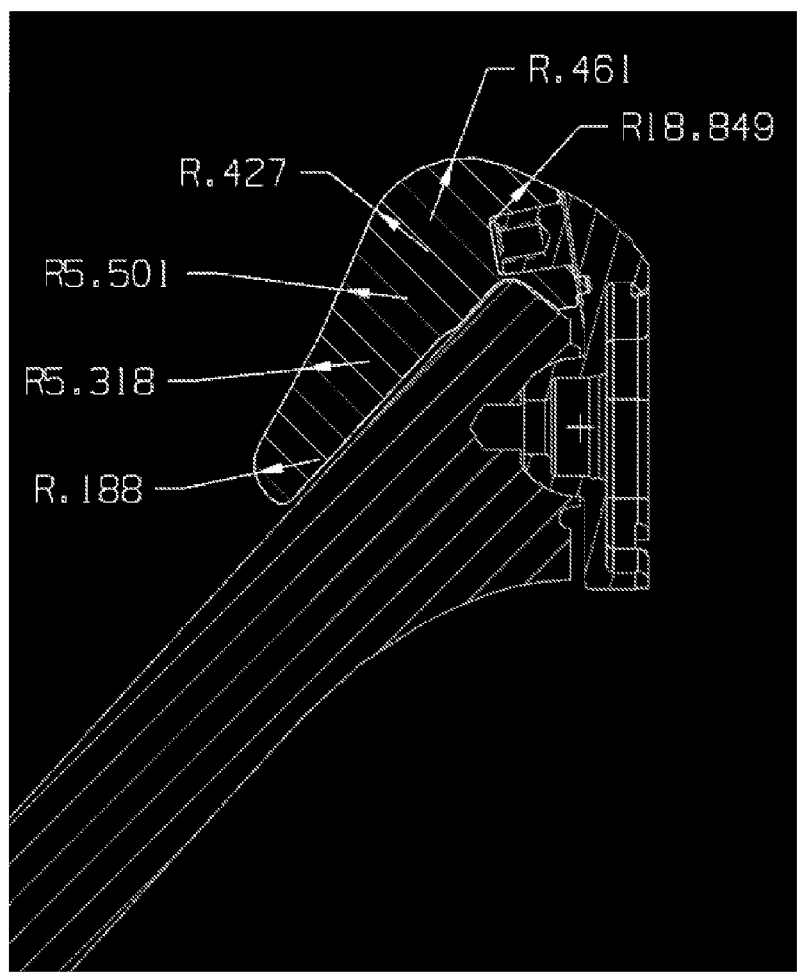
FIG. 12 is a cross-sectional view of an embodiment of a modular humeral adapter tray assembled to a modular tuberosity augment of the present invention showing radii curvatures of the modular tuberosity augment.

FIG. 12 is a cross-sectional view of an embodiment of a modular humeral adapter tray assembled to a modular tuberosity augment of the present invention showing the variable angular curvature of the modular tuberosity augment. In an embodiment, the variable angular curvature produces multiple radii ranging from about 0.1 inches to about 25 inches. In an embodiment, one of the radii ranges from about 17.0 inches to about 19.0 inches at the convex curvature. In an embodiment, this convex curvature established the lateral offset.

Figures 13A, 13B:
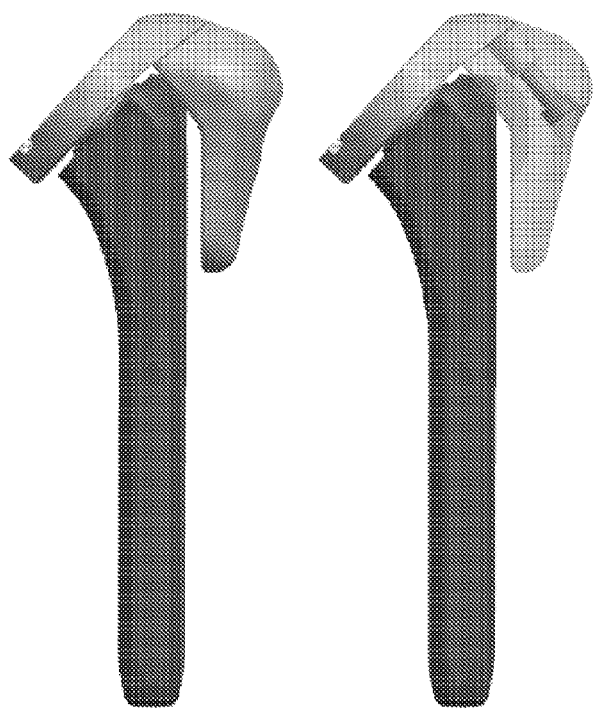
FIGS. 13A and 13B illustrate the modular humeral adapter tray and modular tuberosity augment of FIG. 11 assembled to a humeral stem (FIG. 13B: transparent view depicts cutout of tuberosity and fit around humeral stem lateral fin to provide rotational stability and also facilitate attachment).
Figure 14A:
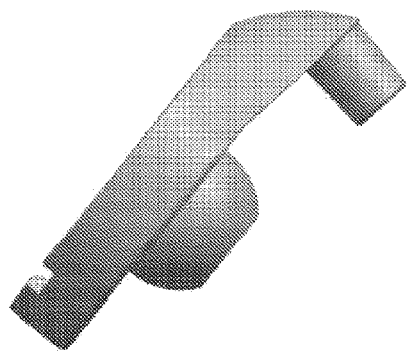
FIGS. 14A-14C illustrate three different views of the modular humeral adapter tray of FIG. 11 with a taper to connect to a modular tuberosity augment (not pictured) of the present invention.
Figure 14B:
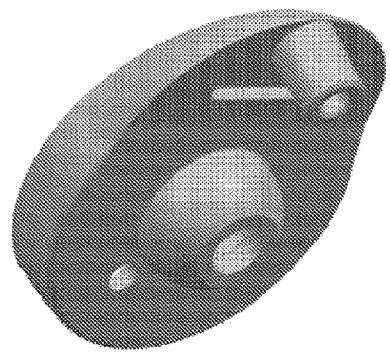
Figure 14C:
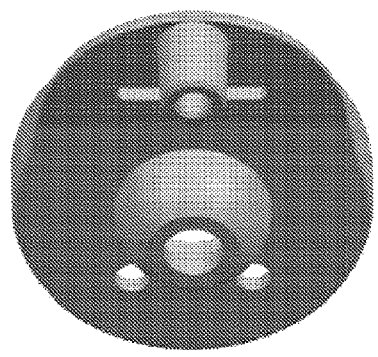
Figure 15A:
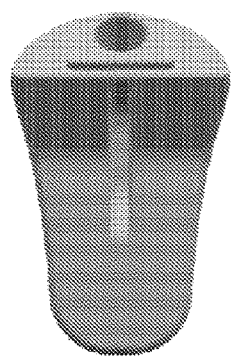
FIGS. 15A-15E illustrate five different views of the modular tuberosity augment of FIG. 11 for connection to a modular humeral adapter tray (not pictured) of the present invention.
Figure 15B:
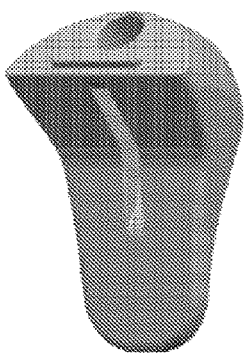
Figure 15C:
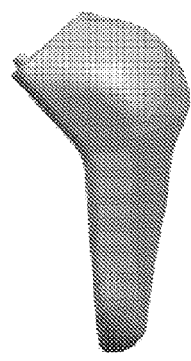
Figure 15D:
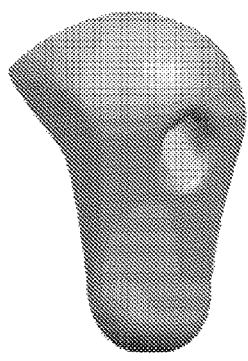
Figure 15E:
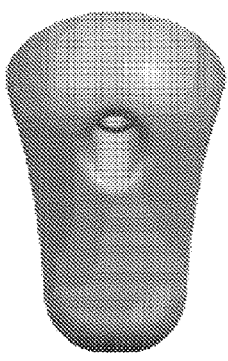

FIGS. 13A and 13B illustrate the modular humeral adapter tray and modular tuberosity augment of FIG. 11 assembled to a humeral stem (FIG. 13B: transparent view depicts cutout of tuberosity and fit around humeral stem lateral fin to provide rotational stability and also facilitate attachment). FIGS. 14A-14C illustrate three different views of the modular humeral adapter tray of FIG. 11 with a taper to connect to a modular tuberosity augment (not pictured) of the present invention. The modular humeral adapter tray also includes a taper for attachment to a humeral stem. FIGS. 15A-15E illustrate five different views of the modular tuberosity augment of FIG. 11 for connection to a modular humeral adapter tray (not pictured) of the present invention. The modular tuberosity augment includes a spherical bore for attachment to the modular humeral adapter tray.

Figures 28A, 28B, 28C:
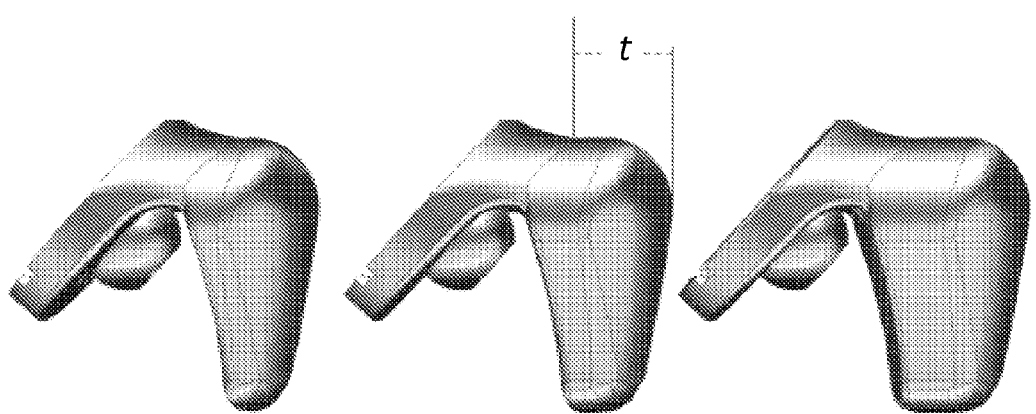
FIGS. 28A-28C illustrate front views of various thickness tuberosity augments of the present invention.
Figure 29A:
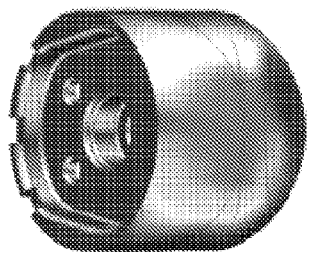
FIGS. 29A-29C illustrate top views of the tuberosity augments of FIGS. 28A-28C.
Figure 29B:
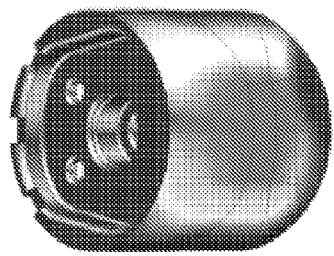
Figure 29C:
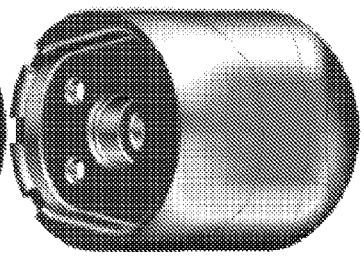

The modular humeral adapter tray of FIGS. 14A-14C can secure to either an Equinoxe® anatomic/revision humeral stem (FIGS. 16A, 16B, 17A, 17B, 18A and 18B) or the Equinoxe® fracture humeral stem (FIGS. 19A, 19B, 20A and 20B) and recreate the shape of the lateral aspect of the proximal humerus in patients with proximal humeral bone loss. It should be noted that the modular humeral adapter tray and modular tuberosity augment of the present invention also permits the surgeon intra-operative flexibility to select any number of shapes or sizes of modular tuberosities. The modular tuberosity augment depicted in FIGS. 15A-15E may be provided in different lengths (FIGS. 21A and 21B) and sizes and/or be provided in different amounts of anterior or posterior coverage (FIGS. 22A-22E) (e.g. the modular tuberosity could extend (or not extend) in any direction (for example, anterior/posterior) to ensure better coverage of the proximal bone defect). For example, such a modular tuberosity augment, as shown in FIGS. 22A-22E, includes an extension portion 2200 providing extended coverage in an anterior or posterior direction. It will be apparent to those of skill in the art, while FIGS. 22A-22E show a modular tuberosity augment having an extension portion 2200 located on one side of the modular tuberosity augment, the extension portion 2200 could instead be located on the opposite side of the modular tuberosity augment. In an embodiment, a tuberosity augment of the present disclosure has a length ranging from about 10 mm to about 80 mm. In an embodiment, a tuberosity augment of the present disclosure has a length ranging from about 15 mm to about 75 mm. In an embodiment, a tuberosity augment of the present disclosure has a length ranging from about 20 mm to about 70 mm. In an embodiment, a tuberosity augment of the present disclosure has a length ranging from about 25 mm to about 65 mm. In an embodiment, a tuberosity augment of the present disclosure has a length ranging from about 30 mm to about 60 mm. In an embodiment, a tuberosity augment of the present disclosure has a length ranging from about 35 mm to about 55 mm. In an embodiment, a tuberosity augment of the present disclosure has a length ranging from about 40 mm to about 50 mm. In an embodiment, a tuberosity augment of the present disclosure has a length of about 40 mm. In an embodiment, a tuberosity augment of the present disclosure has a thickness ranging from about 5 mm to about 50 mm. FIG. 28B illustrates how the thickness "t" of a tuberosity augment is measured. In an embodiment, a tuberosity augment of the present disclosure has a thickness ranging from about 10 mm to about 45 mm. In an embodiment, a tuberosity augment of the present disclosure has a thickness ranging from about 15 mm to about 40 mm. In an embodiment, a tuberosity augment of the present disclosure has a thickness ranging from about 20 mm to about 35 mm. In an embodiment, a tuberosity augment of the present disclosure has a standard thickness of about 20 mm. In an embodiment, a "thin" tuberosity augment of the present disclosure has a standard thickness of about 16 mm. In an embodiment, a "thick" tuberosity augment of the present disclosure has a standard thickness of about 24 mm.

Figures 16A, 16B:
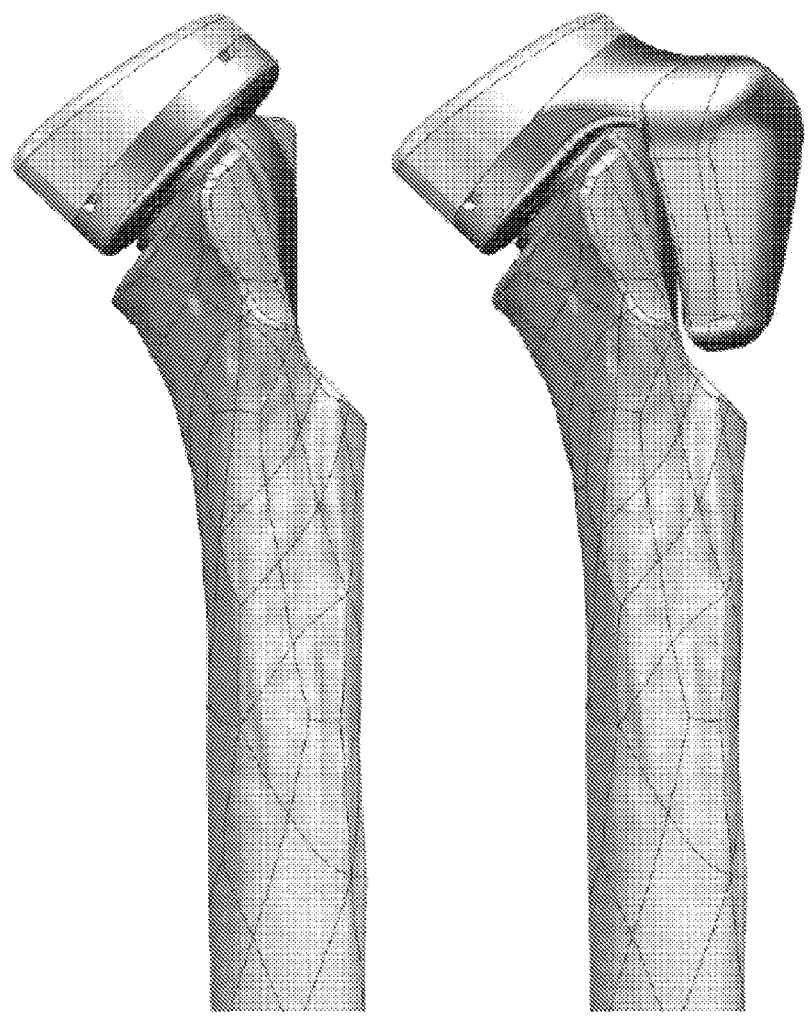
FIGS. 16A and 16B show proximal bone loss in the humerus.

FIGS. 16A and 16B show proximal bone loss in the humerus. FIG. 16A illustrates a humeral adapter tray secured to the Equinoxe® anatomic humeral stem to reconstruct the lateral tuberosity shape/contour in patients with proximal bone loss. FIG. 16B illustrates the monolithic humeral adapter tray with tuberosity augment of FIG. 10 secured to the Equinoxe® anatomic humeral stem to reconstruct the lateral tuberosity shape/contour in patients with proximal bone loss.

Figures 17A, 17B:
FIGS. 17A and 17B illustrate an embodiment of the present invention where the monolithic humeral tray with tuberosity augment of FIG. 10 is secured to the Equinoxe® anatomic humeral stem.
Figures 18A, 18B:
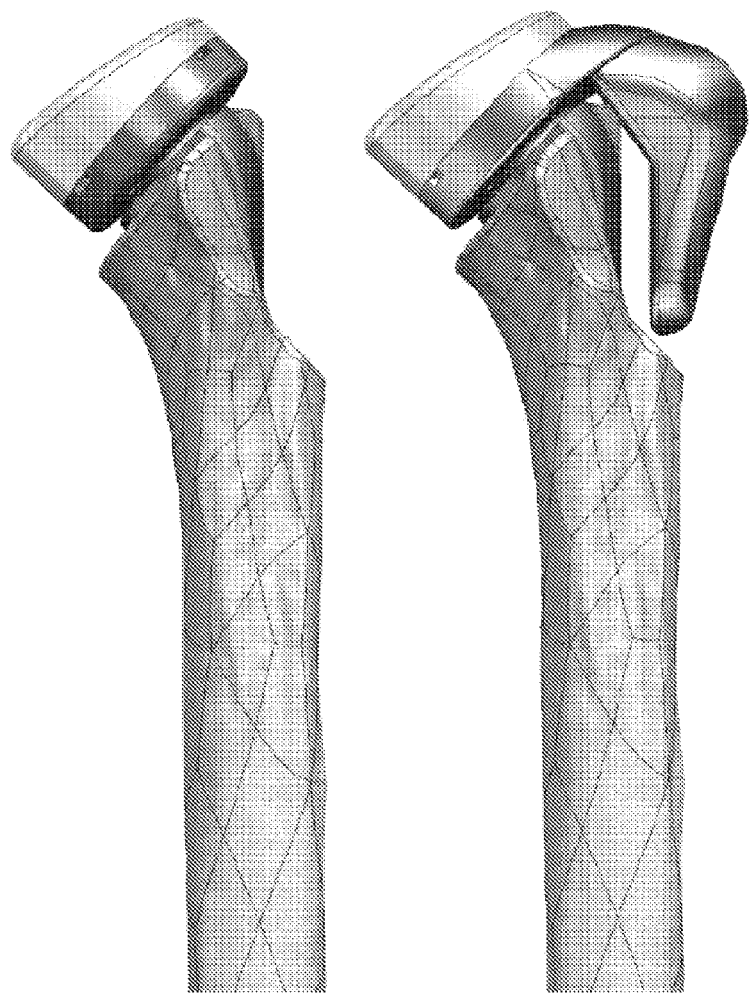
FIGS. 18A and 18B show proximal bone loss in the humerus.

FIGS. 17A and 17B illustrate the monolithic humeral tray with tuberosity augment of FIG. 10 secured to the Equinoxe® anatomic humeral stem. FIG. 17B is a cross-sectional view showing a cutout to permit attachment of the humeral tray to all sizes of humeral stems (from sizes 6 to 17 mm);

FIGS. 18A and 18B show proximal bone loss in the humerus. FIG. 18A illustrate a humeral adapter tray secured to the Equinoxe® anatomic humeral stem to reconstruct the lateral tuberosity shape/contour in patients with proximal bone loss. FIG. 18B illustrates the modular humeral adapter tray/tuberosity augment of FIG. 11 secured to the Equinoxe® anatomic humeral stem to reconstruct the lateral tuberosity shape/contour in patients with proximal bone loss.

Figures 19A, 19B:
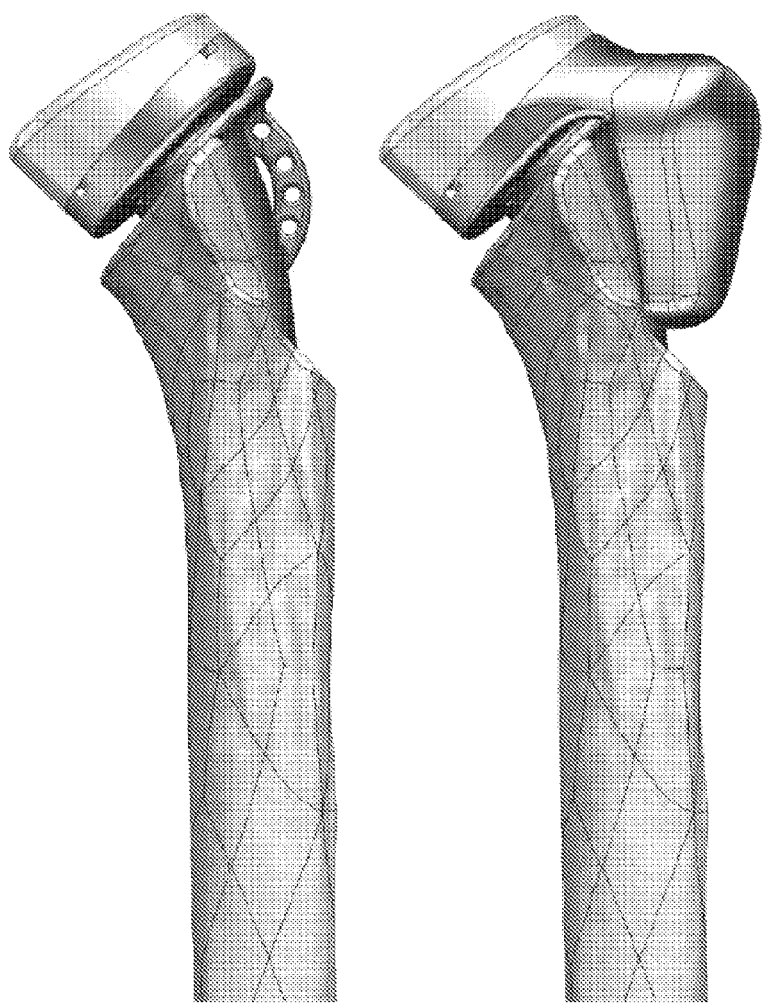
FIGS. 19A and 19B show proximal bone loss in the humerus.

FIGS. 19A and 19B show proximal bone loss in the humerus. FIG. 19A illustrates a humeral adapter tray secured to the Equinoxe® fracture humeral stem to reconstruct the lateral tuberosity shape/contour in patients with proximal bone loss. FIG. 19B illustrates the monolithic humeral adapter tray with tuberosity augment of FIG. 10 secured to the Equinoxe® fracture humeral stem to reconstruct the lateral tuberosity shape/contour in patients with proximal bone loss.

Figures 20A, 20B:
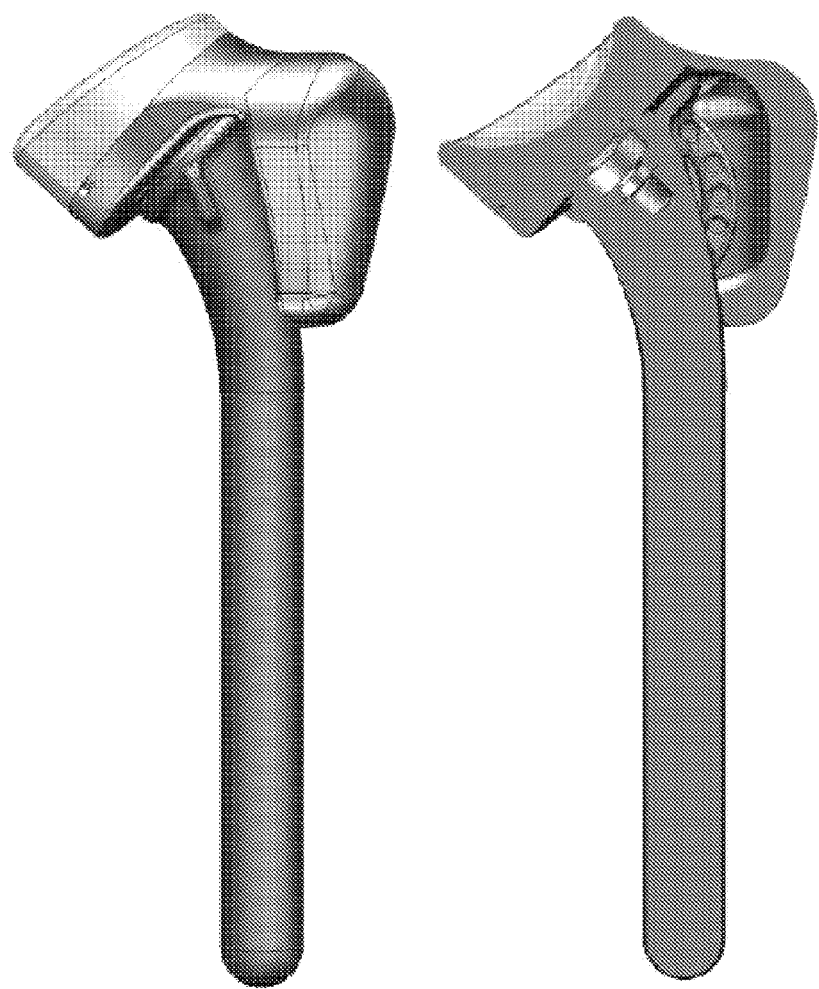
FIGS. 20A and 20B illustrate an embodiment of the present invention where the monolithic humeral tray with tuberosity augment of FIG. 10 is secured to the Equinoxe® fracture humeral stem.

FIGS. 20A and 20B illustrate the monolithic humeral tray with tuberosity augment of FIG. 10 secured to the Equinoxe® fracture humeral stem. FIG. 20B is a cross-sectional view showing a cutout to permit attachment of tray to all sizes of humeral stems (from sizes 6.5 to 12.5 mm).

Figures 21A, 21B:
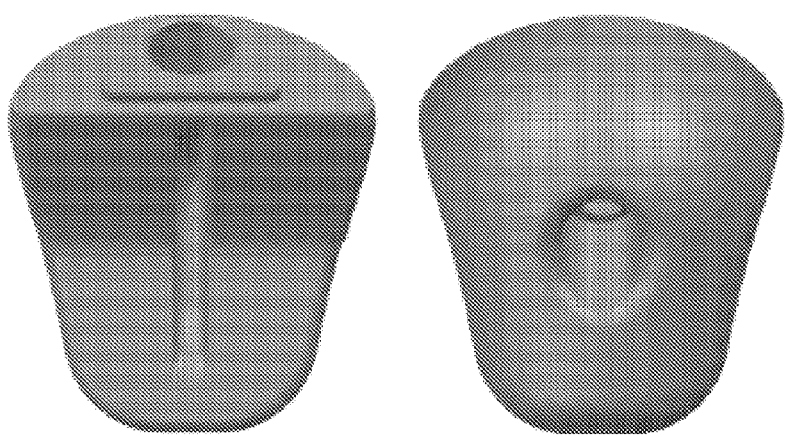
FIGS. 21A and 21B illustrate two different views of an embodiment of a modular tuberosity augment of the present invention for connection to a modular humeral adapter tray (not pictured) of the present invention.

FIGS. 21A and 21B illustrate two different views of an embodiment of a modular tuberosity augment of the present invention for connection to a modular humeral adapter tray (not pictured) of the present invention.

FIGS. 22A-22E illustrate five different views of an embodiment of a modular tuberosity augment of the present invention with additional anterior (or posterior) coverage for connection to a modular humeral adapter tray (not pictured) of the present invention.

Figure 23:
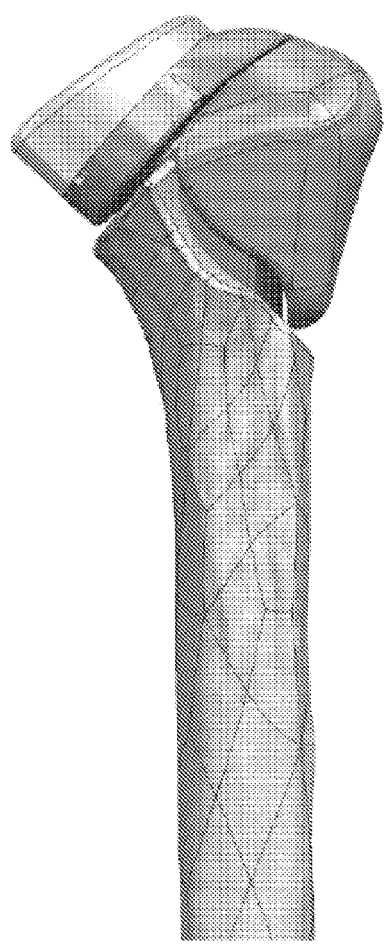
FIG. 23 illustrates an embodiment of the present invention where the modular humeral adapter tray of FIG. 11 with the modular tuberosity augment of FIG. 22 provides additional anterior (or posterior) coverage to reconstruct the lateral tuberosity shape/contour in patients with significant proximal/anterior (or posterior) bone loss.

FIG. 23 illustrates the modular humeral adapter tray of FIG. 11 with the modular tuberosity augment of FIG. 22 with additional anterior (or posterior) coverage to reconstruct the lateral tuberosity shape/contour in patients with significant proximal/anterior (or posterior) bone loss.

As this design may introduce a larger torque on the humeral tray/stem junction, the design of the humeral tray with tuberosity may be designed to accommodate placement of bone cement to better secure it to the humeral stem and/or include screw or suture holes to facilitate placement of screws and/or sutures to ground it to the remaining humeral bone; thereby, off-loading the humeral tray/stem interface and minimizing the transmitted torque.

Figure 24A:
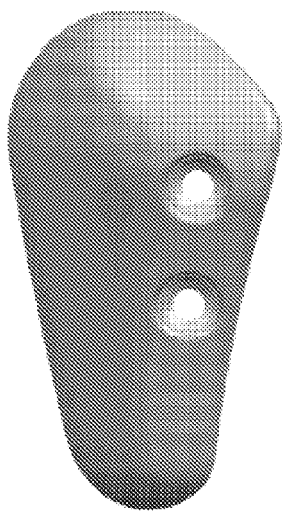
FIGS. 24A-24C illustrate three different views of an embodiment of a modular tuberosity augment of the present invention. Two grooves are present for attachment to an anterior-lateral fin of an Equinoxe® fracture stem (left or right); two screws (not shown) secure the modular tuberosity to the fracture stem anterior-lateral fin.
Figure 24B:
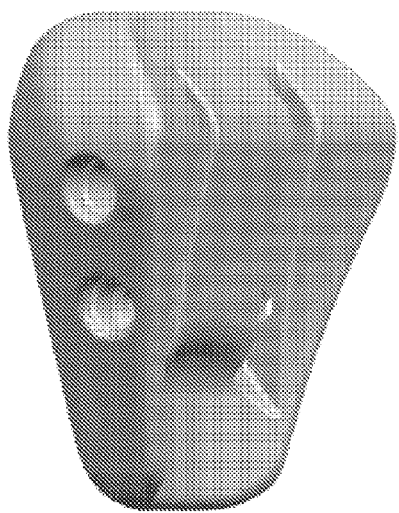
Figure 24C:
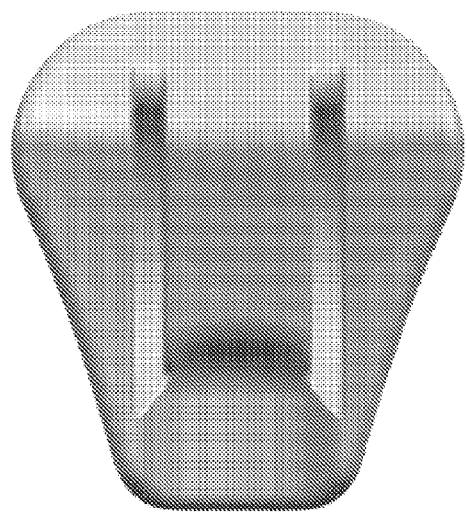
Figure 25:
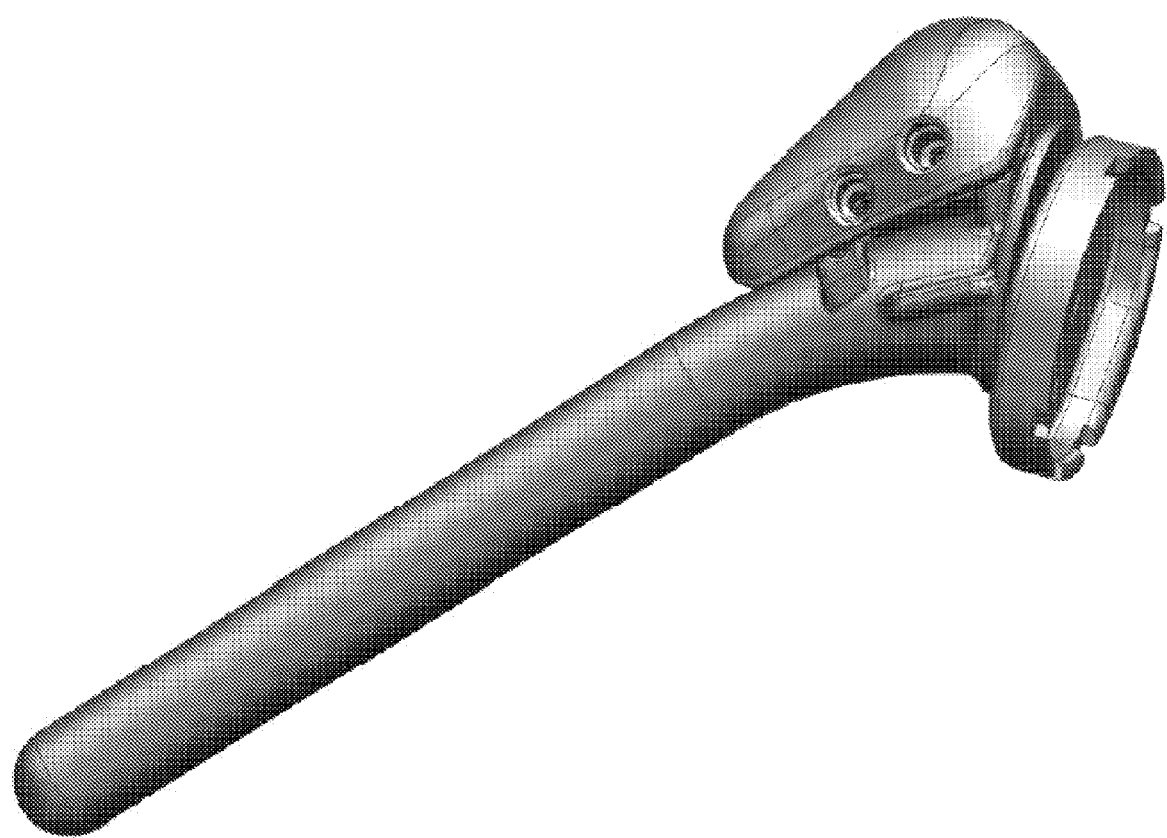
FIG. 25 illustrates an embodiment of a modular tuberosity augment of the present invention secured to the anterior-lateral fin of an Equinoxe® fracture humeral stem.
Figures 26A, 26B:
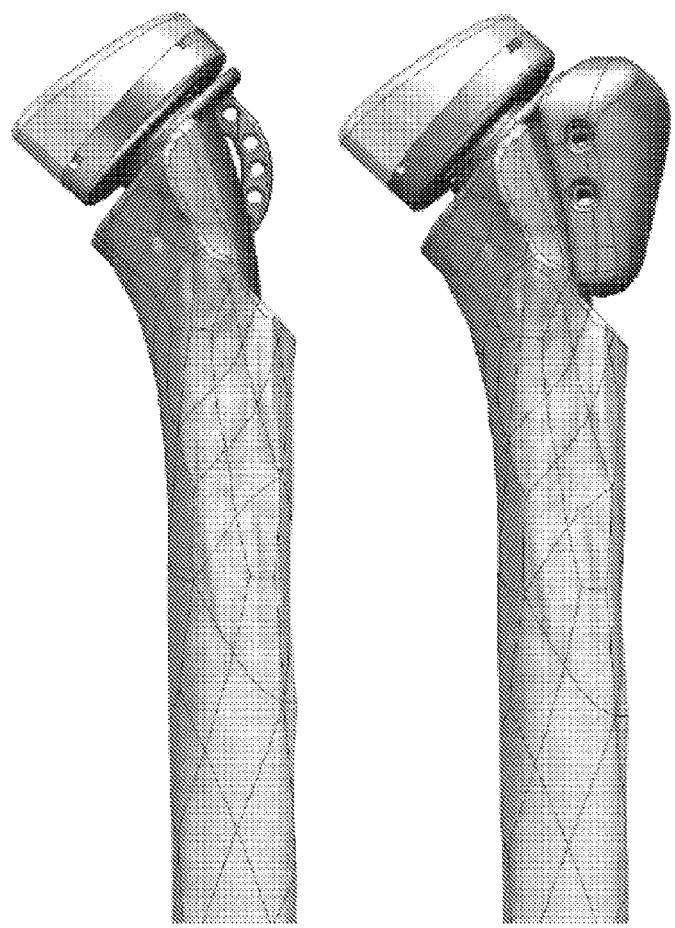
FIGS. 26A and 26B illustrate an embodiment of a modular tuberosity augment of the present invention secured to the lateral fin of an Equinoxe® fracture humeral stem to reconstruct the lateral tuberosity shape/contour in patients with proximal bone loss (particularly in the occurrence of a failed fracture in which the fracture stem is already cemented in-place and the surgeon would want to convert the well-fixed stem to a reverse shoulder).
Figures 27A, 27B:
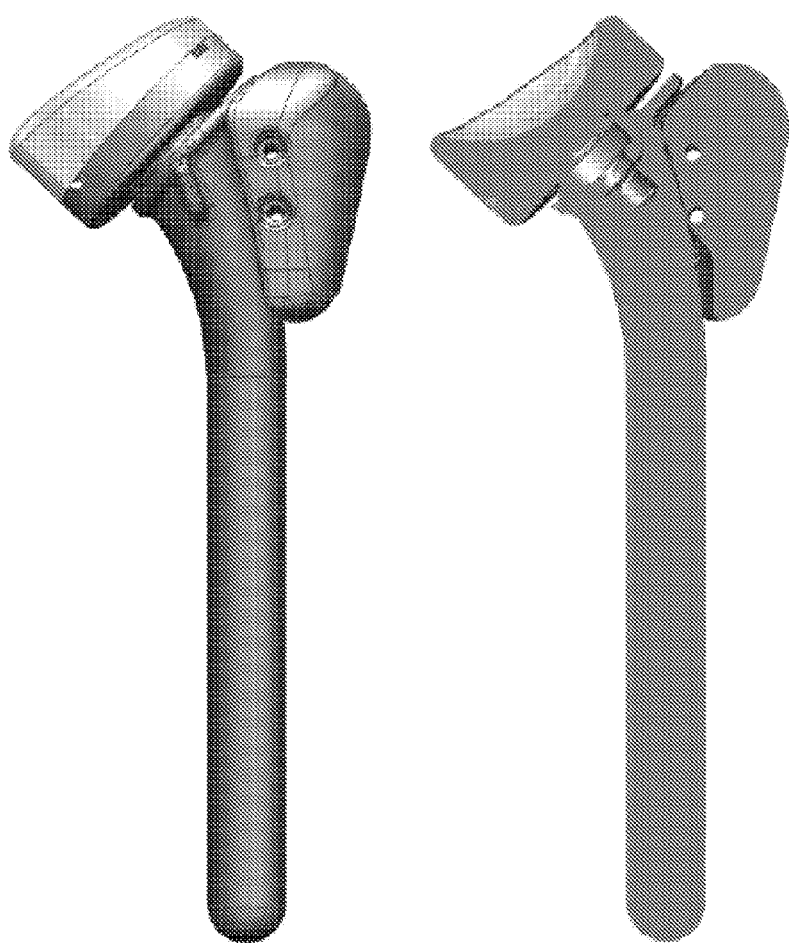
FIGS. 27A and 27B illustrate an embodiment of a modular tuberosity augment of the present invention secured to an Equinoxe® fracture humeral stem. The modular tuberosity augment is sufficiently shaped to permit attachment to all sizes of humeral stems along the lateral humeral fin (from sizes 6.5 to 12.5 mm).

FIGS. 24A-24C illustrate an embodiment of a modular tuberosity augment of the present invention in which two grooves are present for attachment to an anterior-lateral fin of an Equinoxe® fracture stem (left or right); two screws (not shown) secure the modular tuberosity to the fracture stem anterior-lateral fin. The modular tuberosity augment of FIGS. 24A-24C and FIG. 25 secures to the lateral fin of the Equinoxe® fracture humeral stem (FIGS. 26A and 26B and FIGS. 27A and 27B) to recreate the shape of the lateral aspect of the proximal humerus in patients with proximal humeral bone loss. It should be noted that this type of modular tuberosity augment does not necessarily need to attach directly to the lateral fin of the humeral stem, it may modularly or rigidly attach, for example, with screws or cables to any portion of a lateral humeral stem for this intended use.

In an embodiment, by recreating the shape/contour of the proximal humeral bone with a device of the present invention, both function and stability is improved with reverse shoulder arthroplasty in patients with proximal humeral bone loss. In an embodiment, reproducing this lateral tuberosity shape/contour addresses cosmetic concerns and reduces the probability of deltoid scarring by restoring a smooth surface for the deltoid to slide/articulate against (instead of the rough surface of the stem/jagged unresorbed bone—which could abrade the muscle). As a result, a device of the present invention is typically provided as a highly-polished (electropolished) implant in order to minimize any muscle abrasion as the muscle glides over this artificial tuberosity. In an embodiment, by restoring the lateral contour of the proximal humerus, a device of the present invention increases the wrapping of the deltoid around the humerus to impart joint compression at greater levels of elevation (as described in Table 1 and below in Table 2) and also increases the abductor moment arm of the deltoid (increasing the efficiency of the muscle thereby requiring less deltoid force to elevate the arm) while maintaining these increased moment arms at greater levels of elevation (avoiding the decrease in the abductor moment arm with increased elevation as described in FIGS. 8A-8D).

The shape/thickness of a tuberosity augment of the present invention can be provided in varying thicknesses or shapes. (FIGS. 28A-28C and FIGS. 29A-29C). Specifically, a tuberosity augment of the present invention can be provided in multiple thickness (some that are even more lateral than anatomic) in order to strategically tension a joint intraoperatively (to further increase deltoid tension and further increase deltoid wrapping and the deltoid abductor moment arm). Additionally, the shape of a tuberosity augment of the present invention could be offered in various curvatures or have a curvature that is cam-shaped (or biased in one particular direction, be it posterior or anterior) to recruit more of a muscle to a given motion. In an embodiment, a tuberosity augment of the present disclosure has a thickness ranging from about 5 mm to about 50 mm. FIG. 28B illustrates how the thickness "t" of a tuberosity augment is measured. In an embodiment, a tuberosity augment of the present disclosure has a thickness ranging from about 10 mm to about 45 mm. In an embodiment, a tuberosity augment of the present disclosure has a thickness ranging from about 15 mm to about 40 mm. In an embodiment, a tuberosity augment of the present disclosure has a thickness ranging from about 20 mm to about 35 mm. In an embodiment, a tuberosity augment of the present disclosure has a standard thickness of about 20 mm. In an embodiment, a "thin" tuberosity augment of the present disclosure has a standard thickness of about 16 mm. In an embodiment, a "thick" tuberosity augment of the present disclosure has a standard thickness of about 24 mm.

Figure 30:
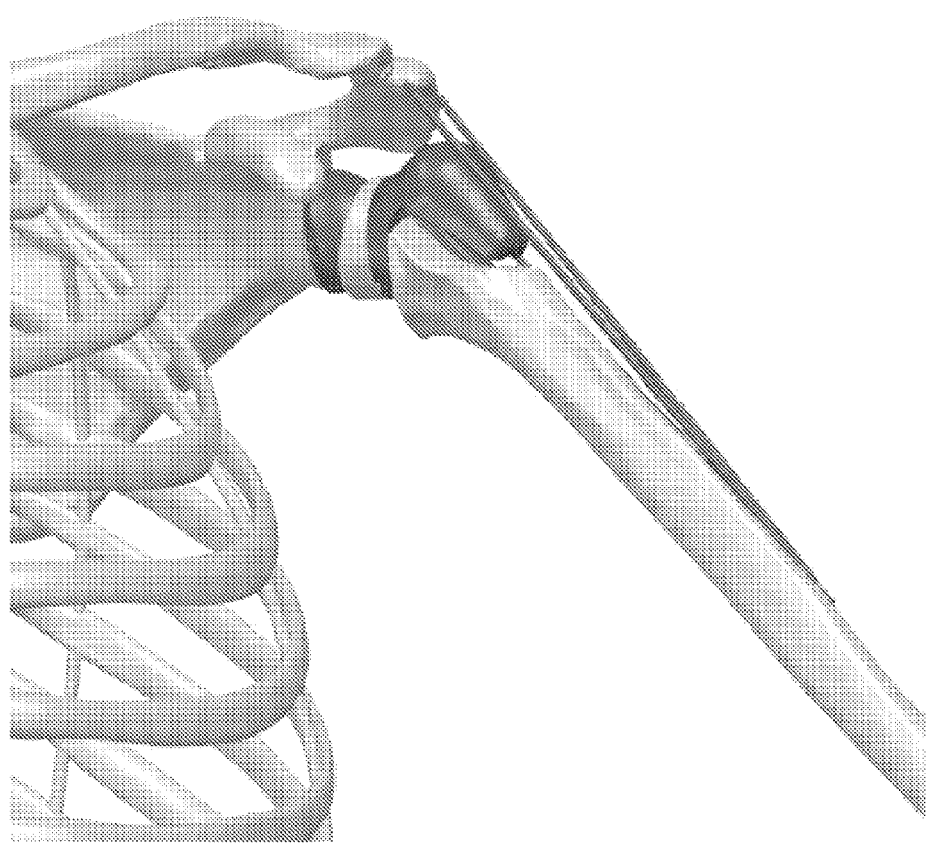
FIG. 30 is a computer model of a 38 mm Equinoxe® reverse shoulder with a humeral tray tuberosity of the present invention (standard thickness) abducted to 46 degrees relative to a fixed scapula in which the middle deltoid no longer wraps the tuberosity augment and therefore no longer imparts a stabilizing compressive force to the glenoid.
Figure 31:
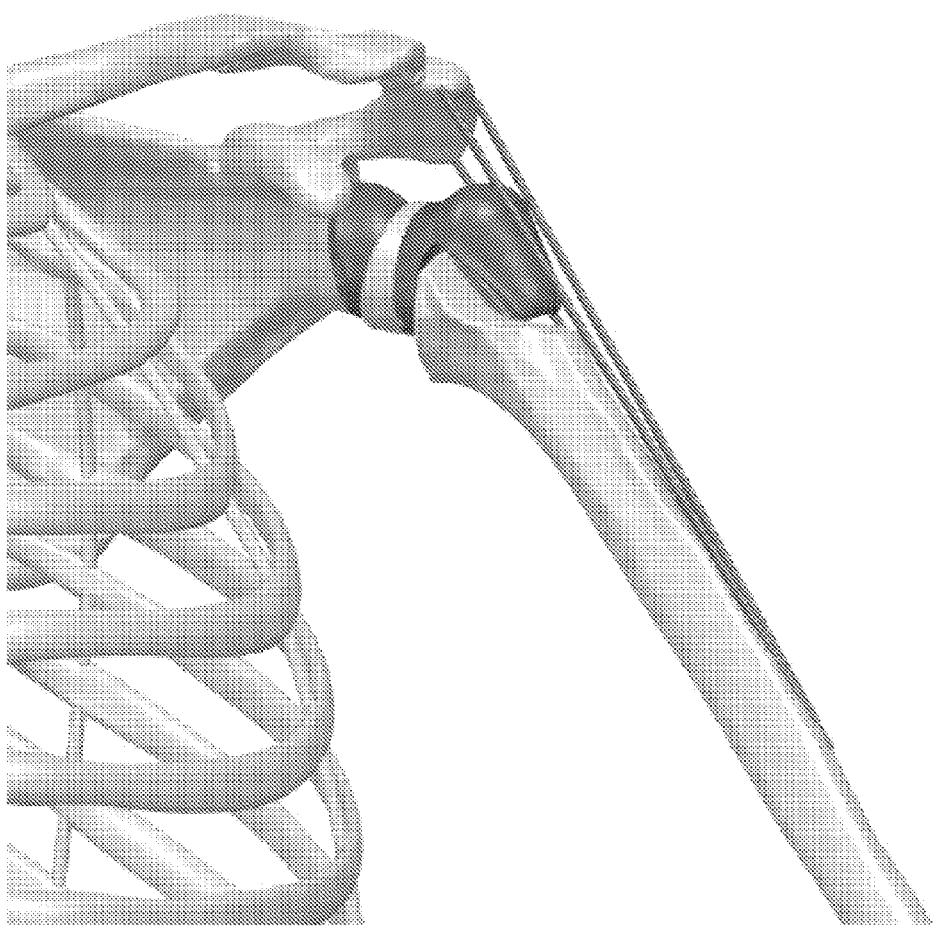
FIG. 31 is a computer model of a 38 mm Equinoxe® reverse shoulder with a humeral tray tuberosity of the present invention (−4 mm thickness) abducted to 36 degrees relative to a fixed scapula in which the middle deltoid no longer wraps the tuberosity augment and therefore no longer imparts a stabilizing compressive force to the glenoid.
Figure 32:
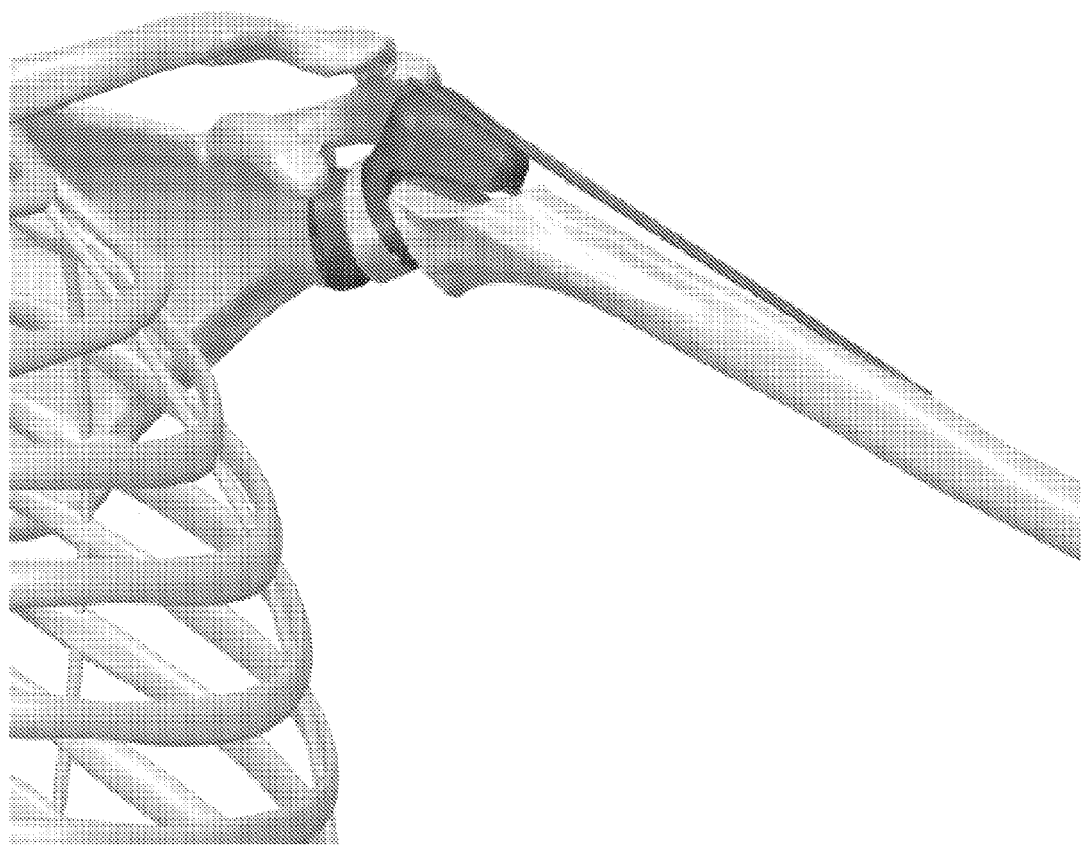
FIG. 32 is a computer model of a 38 mm Equinoxe® reverse shoulder with a humeral tray tuberosity of the present invention (+4 mm thickness) abducted to 66 degrees relative to a fixed scapula in which the tuberosity augment impinged on the acromion (at this level of elevation the middle deltoid still wrapped the tuberosity augment and therefore still imparted a stabilizing compressive force to the glenoid).

As described in Table 2, deltoid wrapping can be increased in the presence of a proximal humeral bone loss with the use of a tuberosity augment of the present invention. The amount of deltoid wrapping can be selected based upon the thickness of humeral tray tuberosity augment chosen (to intra-operatively tension a joint), where thicker tray tuberosities result in greater wrapping. Specifically, the addition of the standard thickness augment (an augment having a thickness, in an embodiment, of 20 mm) with proximal humeral bone loss increased the deltoid wrapping for the 38 mm Equinoxe® from 20 to 46°, see FIG. 6 and FIG. 30. When the augment is 4 mm thinner than the standard and used with proximal humeral bone loss, deltoid wrapping is increased for the 38 mm Equinoxe® from 20 to 36°, see FIG. 6 and FIG. 31. When the augment is 4 mm thicker than the standard and used with proximal humeral bone loss, deltoid wrapping is increased for the 38 mm Equinoxe® from 20 to 66°, see FIG. 6 and FIG. 32.

TABLE 2

Wrapping of Middle Deltoid around Humeral Tray Tuberosity Augments of the Present Disclosure

| | Abduction where deltoid doesn't wrap lateral humerus/tuberosity augment |
|---|---|
| 38 mm Equinoxe, 20° retroversion with Proximal Humeral Bone Loss (FIG. 6) | 20° |
| 38 mm Equinoxe with Standard Tuberosity Augment, 20° retroversion with Proximal Humeral Bone Loss (FIG. 30) | 46° |
| 38 mm Equinoxe with −4 mm Tuberosity Augment, 20° retroversion with Proximal Humeral Bone Loss (FIG. 31) | 36° |
| 38 mm Equinoxe with +4 mm Tuberosity Augment, 20° retroversion with Proximal Humeral Bone Loss (FIG. 32) | 66° (impingement; middle deltoid still wrapped at this degree of elevation) |

Figure 33:
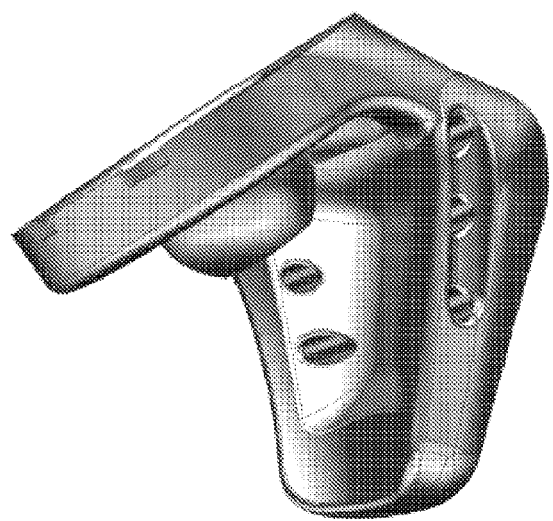
FIG. 33 illustrates an embodiment of a tuberosity augment of the present invention with suture holes on anterior/posterior sides to facilitate attachment of rotator cuff muscles.

Additionally, a monolithic humeral adapter tray/tuberosity augment of the present invention or a modular humeral adapter tray/tuberosity augment of the present invention can include soft tissue attachment features (e.g. sutures) or special coatings to facilitate reattachment of the rotator cuff or other muscle desired by the surgeon to be transferred in order to reattach those muscle(s) to the anterior or posterior proximal humerus so that the action of the muscles induce active internal or external rotation (FIG. 33).

A device of the present invention can be manufactured from different biocompatible materials, including Co—Cr, stainless steel, titanium, carbon fiber, ceramic, PMMA bone cement, pyrocarbon, and/or bone graft. In an embodiment, a tuberosity of the present invention is manufactured from Ti-6Al-4V. Additionally, a device of the present invention can be surface coated or treated with various processes to encourage fixation to the muscle and/or bone. A device of the present invention may connect directly to the bone, muscle, or humeral stem and may include various posts, screws (locking/compression/or poly-axial locking), fins, and or cables/sutures at various angles and positions to facilitate attachment of the augment to each aforementioned location on the humerus (which may or may not include a humeral stem in the intramedullary canal). Humeral stems of known shoulder prosthesis designs can be adapted to accept a modular tuberosity of the present invention.

A monolithic humeral adapter tray/tuberosity augment of the present invention or a modular humeral adapter tray/tuberosity augment of the present invention may be provided in a kit. Further, a kit of the present invention may provide multiple monolithic humeral adapter trays/tuberosity augments or multiple modular humeral adapter trays/tuberosity augments which vary with respect to their lengths and thicknesses. A kit of the present invention may further include at least one of posts, locking/compression screws, poly-axial locking screws, fins, cables, sutures and/or instructions.

The medical and healthcare sector represents one of the strongest vertical markets for applications of additive manufacturing (AM) and 3D printing (3DP) in which minuscule grains of plastic are sprayed in overlapping layers at high temperature and pressure to produce exquisitely precise, personalized, and complex prosthesis. In an embodiment, a Digital Imaging and Communications in Medicine (DICOM) file from a computed tomography (CT) scan or a magnet resonance imagining (MM) scan of a patient's lateral humerus site can be converted into an STL file which can then be 3D printed. The 3D print can help visualize the lateral humerus site and plan an augment procedure of the present invention. This process can allow a surgeon to experience an extra dimension when planning an augment procedure, and the ability to fully manipulate and explore the area of interest (lateral humerus) in the real world before commencing surgery. To create an anatomically correct tuberosity augment of the present invention, MRI scans and CT scans can be utilized to design and build the prostheses prior to any surgery being carried out.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following description.

What is claimed is:

1. A kit, comprising:
   a. a humeral stem configured to attach to a bone; and
   b. a plurality of prosthetic augments,
      wherein each individual prosthetic augment within the plurality includes:
         a humeral adapter tray portion configured to connect a humeral liner to the humeral stem, and
         an augment portion configured to reconstruct a lateral tuberosity shape of a humerus, having a lateral face adapted for contacting an underside of a muscle, wherein at least a portion of the lateral face includes a bulbous surface adapted to alter a wrapping angle of the muscle around the lateral tuberosity to a degree, wherein the lateral face has a radius of curvature selected from one of a constant radius of curvature or a variable radius of curvature, and wherein the lateral face includes a continuously smoothly curved surface that (1)

extends from a first end that abuts the humeral adapter tray, and (2) is contiguous with a surface of the humeral adapter tray.

2. The kit of claim 1, wherein each individual prosthetic augment within the plurality are monolithic.

3. The kit of claim 1, wherein the humeral adapter tray portion and the augment portion of each individual prosthetic augment within the plurality are modular and are configured to lockingly engage each other.

4. The kit of claim 1, wherein each individual prosthetic augment within the plurality is further configured to include suture bores for soft tissue fixation.

5. The kit of claim 1, wherein each individual prosthetic augment within the plurality is coated to facilitate muscle reattachment.

6. The kit of claim 1, wherein an individual augment portion within the plurality of prosthetic augments is further configured to include at least one of additional anterior coverage or additional posterior coverage, wherein the additional anterior coverage or additional posterior coverage is configured to reconstitute the lateral tuberosity.

7. The kit of claim 1, wherein the humeral stem is a revision humeral stem.

8. The kit of claim 1, wherein the humeral stem is a fracture humeral stem.

9. The kit of claim 1, wherein at least one screw hole extends through the augment portion.

10. The kit device of claim 1, wherein the augment portion of each individual prosthetic augment within the plurality further comprises a medial face opposite the lateral face, and wherein the medial face of each individual prosthetic augment within the plurality is adapted for contacting the humeral stem.

11. A prosthetic device,
wherein the prosthetic device is modular and comprises:
a. a humeral stem configured to attach to a bone; and
b. a prosthetic augment, comprising
a humeral adapter tray portion configured to connect a humeral liner to the humeral stem, and
an augment portion configured to reconstruct a lateral tuberosity shape of a humerus, having a lateral face adapted for contacting an underside of a muscle, wherein at least a portion of the lateral face includes a bulbous surface adapted to alter a wrapping angle of the muscle around the lateral tuberosity to a degree, wherein the lateral face has a radius of curvature selected from one of a constant radius of curvature or a variable radius of curvature, and wherein the lateral face includes a continuously smoothly curved surface that (1) extends from a first end that abuts the humeral adapter tray, and (2) is contiguous with a surface of the humeral adapter tray.

12. The prosthetic device of claim 11, wherein the prosthetic augment is monolithic.

13. The prosthetic device of claim 11, wherein the humeral adapter tray portion and the augment portion are modular and are configured to lockingly engage each other.

14. The prosthetic device of claim 11, wherein the prosthetic augment is further configured to include suture bores for soft tissue fixation.

15. The prosthetic device of claim 11, wherein the prosthetic augment is coated to facilitate muscle reattachment.

16. The prosthetic device of claim 11, wherein the augment portion is further configured to include at least one of additional anterior coverage or additional posterior coverage, wherein the additional anterior coverage or additional posterior coverage is configured to reconstitute the lateral tuberosity.

17. The prosthetic device of claim 11, wherein the humeral stem is a revision humeral stem.

18. The prosthetic device of claim 11, wherein the humeral stem is a fracture humeral stem.

19. The prosthetic device of claim 11, wherein at least one screw hole extends through the augment portion.

20. The prosthetic device of claim 11, wherein the augment portion further comprises a medial face opposite the lateral face, and wherein the medial face is adapted for contacting the humeral stem.

* * * * *